US008623851B2

(12) United States Patent  
Banerjee et al.

(10) Patent No.: US 8,623,851 B2
(45) Date of Patent: *Jan. 7, 2014

(54) FORMOTEROL/STEROID BRONCHODILATING COMPOSITIONS AND METHODS OF USE THEREOF

(75) Inventors: Partha S. Banerjee, Wynnewood, PA (US); Imtiaz A. Chaudry, American Canyon, CA (US); Stephen Pham, Sacramento, CA (US)

(73) Assignee: Mylan Specialty L.P., Basking Ridge, NJ (US)

( * ) Notice: Subject to any disclaimer, the term of this patent is extended or adjusted under 35 U.S.C. 154(b) by 596 days.

This patent is subject to a terminal disclaimer.

(21) Appl. No.: 12/625,328

(22) Filed: Nov. 24, 2009

(65) Prior Publication Data

US 2010/0069342 A1 Mar. 18, 2010

Related U.S. Application Data

(60) Continuation of application No. 10/145,978, filed on May 13, 2002, now abandoned, and a division of application No. 09/887,496, filed on Jun. 22, 2001, now abandoned.

(60) Provisional application No. 60/284,607, filed on Apr. 17, 2001.

(51) Int. Cl.
*A61K 31/58* (2006.01)
*A61K 31/135* (2006.01)
*A61K 9/00* (2006.01)

(52) U.S. Cl.
USPC .......................... 514/173; 514/653; 424/400

(58) Field of Classification Search
USPC ................................. 514/173, 653
See application file for complete search history.

(56) References Cited

U.S. PATENT DOCUMENTS

| | | |
|---|---|---|
| 3,929,768 A | 12/1975 | Brattsand et al. |
| 3,994,974 A | 11/1976 | Murakami et al. |
| 4,335,121 A | 6/1982 | Philipps et al. |
| 4,992,474 A | 2/1991 | Skidmore et al. |
| 5,033,252 A | 7/1991 | Carter |
| 5,052,558 A | 10/1991 | Carter |
| 5,126,375 A | 6/1992 | Skidmore et al. |
| 5,225,445 A | 7/1993 | Skidmore et al. |
| 5,270,305 A | 12/1993 | Palmer |
| 5,275,212 A * | 1/1994 | Moris ........................ 141/3 |
| 5,290,815 A | 3/1994 | Johnson et al. |
| 5,323,907 A | 6/1994 | Kalvelage |
| 5,525,623 A | 6/1996 | Spear et al. |
| 5,602,110 A | 2/1997 | Drumm et al. |
| 5,654,276 A | 8/1997 | Barrett et al. |
| 5,668,110 A | 9/1997 | Barrett et al. |
| 5,674,860 A | 10/1997 | Carling et al. |
| 5,677,280 A | 10/1997 | Barrett et al. |
| 5,677,809 A | 10/1997 | Kadlec |
| 5,683,983 A | 11/1997 | Barrett et al. |
| 5,691,336 A | 11/1997 | Dorn et al. |
| 5,733,526 A | 3/1998 | Trevino et al. |
| 5,750,549 A | 5/1998 | Caldwell et al. |
| 5,780,467 A | 7/1998 | Dorn et al. |
| 5,795,564 A | 8/1998 | Aberg et al. |
| 5,874,063 A | 2/1999 | Briggner et al. |
| 5,874,481 A | 2/1999 | Weers et al. |
| 5,877,191 A | 3/1999 | Caldwell et al. |
| 5,929,094 A | 7/1999 | Durette et al. |
| 5,965,622 A | 10/1999 | Senanayake |
| 5,972,919 A | 10/1999 | Carling et al. |
| 5,980,949 A | 11/1999 | Trofast |
| 5,983,956 A | 11/1999 | Trofast |
| 6,004,537 A | 12/1999 | Blondino et al. |
| 6,030,604 A | 2/2000 | Trofast |
| 6,040,344 A | 3/2000 | Gao et al. |
| 6,041,777 A | 3/2000 | Faithfull et al. |
| 6,068,833 A | 5/2000 | Aberg et al. |
| 6,071,971 A | 6/2000 | Senanayake |
| 6,126,919 A | 10/2000 | Stefely et al. |
| 6,136,603 A | 10/2000 | Dean et al. |
| 6,150,418 A | 11/2000 | Hochrainer et al. |
| 6,161,536 A | 12/2000 | Redmon et al. |
| 6,235,725 B1 | 5/2001 | Ahmed |
| 6,261,539 B1 | 7/2001 | Adjei et al. |
| 6,287,540 B1 | 9/2001 | Trofast |
| 6,303,145 B2 | 10/2001 | Jerussi et al. |
| 6,369,115 B1 | 4/2002 | Ward |

(Continued)

FOREIGN PATENT DOCUMENTS

| | | |
|---|---|---|
| DE | 2305092 | 2/1973 |
| DE | 19541689 | 5/1996 |

(Continued)

OTHER PUBLICATIONS

West, Solid state chemistry and its application, Wilsy, New York, 1988. pp. 358, 365.*
Vippagunta et al. "Crystalline solid," Advanced, drug, Delivery, 2001, vol. 48, pp. 3-26.*
Ulrich "Crystallization," Chapter 4, Kirk-Othmer Encyclopedia of Chemical techology, John, Wiley and Sons, 2002.*
Bartow and Broagden "An update of its Pharmaceutical properties and therapeutic efficacy in management of asthma," Drugs, 1998, vol. 55, No. 2, pp. 303-322.*
Remington's Pharmaceutical Sciences, Seventeeth Edition, 1985, pp. 1455-1472.*
Barnes, "Scientific rationale for inhaled combination therapy with long-acting b2-agonists and corticosteroids," Eur. Respir. J, 19:182-191 (2002).

(Continued)

*Primary Examiner* — Shengjun Wang
(74) *Attorney, Agent, or Firm* — McDermott Will & Emery LLP

(57) ABSTRACT

Bronchodilating compositions and methods are provided. The compositions are intended for administration as a nebulized aerosol. In certain embodiments, the compositions contain formoterol, or a derivative thereof, and a steroidal anti-inflammatory agent. Methods for treatment, prevention, or amelioration of one or more symptoms of bronchoconstrictive disorders using the compositions provided herein are also provided.

89 Claims, No Drawings

(56) References Cited

U.S. PATENT DOCUMENTS

| | | | |
|---|---|---|---|
| 6,448,296 B2 * | 9/2002 | Yasueda et al. | 514/781 |
| 6,461,591 B1 | 10/2002 | Keller et al. | |
| 6,481,435 B2 | 11/2002 | Hochrainer et al. | |
| 6,667,344 B2 | 12/2003 | Banerjee et al. | |
| 6,814,953 B2 | 11/2004 | Banerjee et al. | |
| 7,070,800 B2 | 7/2006 | Bechtold-Peters | |
| 7,348,362 B2 * | 3/2008 | Banerjee et al. | 514/651 |
| 7,462,645 B2 * | 12/2008 | Chaudry et al. | 514/653 |
| 7,473,710 B2 * | 1/2009 | Chaudry et al. | 514/653 |
| 7,541,385 B2 * | 6/2009 | Chaudry et al. | 514/653 |
| 8,114,912 B2 * | 2/2012 | Chaudry et al. | 514/651 |
| 2001/0024641 A1 | 9/2001 | Yang | |
| 2002/0032149 A1 | 3/2002 | Kensey | |
| 2002/0061835 A1 | 5/2002 | Kensey | |
| 2002/0081266 A1 | 6/2002 | Woolfe et al. | |
| 2002/0099013 A1 | 7/2002 | Piccariello et al. | |
| 2002/0103260 A1 | 8/2002 | Clarke et al. | |
| 2002/0151597 A1 | 10/2002 | Banerjee et al. | |
| 2002/0151598 A1 | 10/2002 | Banerjee et al. | |
| 2002/0183293 A1 | 12/2002 | Banerjee | |
| 2003/0055026 A1 | 3/2003 | Banerjee et al. | |
| 2003/0109510 A1 | 6/2003 | Gavin | |

FOREIGN PATENT DOCUMENTS

| | | |
|---|---|---|
| DE | 19835346 | 2/2000 |
| DE | 19847970 | 4/2000 |
| EP | 0 370 632 | 10/1989 |
| EP | 0616 525 B1 | 9/1995 |
| EP | 1 157 689 | 11/2001 |
| EP | 1 229 034 | 8/2002 |
| EP | 1 236 467 | 9/2002 |
| WO | WO 93/11773 | 6/1993 |
| WO | WO 95/05805 | 3/1995 |
| WO | WO 95/31964 | 11/1995 |
| WO | WO 96/18384 | 6/1996 |
| WO | WO 96/19198 | 6/1996 |
| WO | WO 96/19968 | 7/1996 |
| WO | WO 96/32095 | 10/1996 |
| WO | WO 97/47286 | 12/1997 |
| WO | WO 98/05302 | 2/1998 |
| WO | WO 98/15280 | 4/1998 |
| WO | WO 98/31351 | 7/1998 |
| WO | WO 98/31352 | 7/1998 |
| WO | WO 98/34595 | 8/1998 |
| WO | WO 98/34596 | 8/1998 |
| WO | WO 98/41193 | 9/1998 |
| WO | WO 99/00134 | 1/1999 |
| WO | 99/17754 | 4/1999 |
| WO | WO 99/15182 | 4/1999 |
| WO | WO 99/25359 | 5/1999 |
| WO | WO 99/30703 | 6/1999 |
| WO | WO 99/36095 | 7/1999 |
| WO | WO 99/40939 | 8/1999 |
| WO | WO 99/48476 | 9/1999 |
| WO | WO 99/61003 | 12/1999 |
| WO | WO 99/65464 | 12/1999 |
| WO | WO 00/00181 | 1/2000 |
| WO | WO 00/06121 | 2/2000 |
| WO | WO 00/07567 | 2/2000 |
| WO | WO 00/16814 | 3/2000 |
| WO | WO 00/23037 | 4/2000 |
| WO | WO 00/23065 | 4/2000 |
| WO | WO 00/28979 | 5/2000 |
| WO | WO 00/03613 | 6/2000 |
| WO | WO 00/30612 | 6/2000 |
| WO | WO 00/33892 | 6/2000 |
| WO | 00/47200 | 8/2000 |
| WO | WO 00/47200 | 8/2000 |
| WO | WO 00/48587 | 8/2000 |
| WO | WO 00/51591 | 8/2000 |
| WO | 00/51591 | 9/2000 |
| WO | WO 00/53187 | 9/2000 |
| WO | WO 00/53188 | 9/2000 |
| WO | WO 01/22956 | 4/2001 |
| WO | WO 01/27107 | 4/2001 |
| WO | WO 01/32163 | 5/2001 |
| WO | 01/39745 | 6/2001 |
| WO | WO 01/39745 | 6/2001 |
| WO | WO 01/54664 | 8/2001 |
| WO | WO 01/70198 | 9/2001 |
| WO | 01/78745 | 10/2001 |
| WO | WO 01/78735 | 10/2001 |
| WO | WO 01/78737 | 10/2001 |
| WO | WO 01/78745 | 10/2001 |
| WO | WO 01/85137 | 11/2001 |
| WO | WO 01/89491 | 11/2001 |
| WO | WO 01/89492 | 11/2001 |
| WO | WO 02/03958 | 1/2002 |
| WO | WO 02/07672 | 1/2002 |
| WO | WO 02/11803 | 2/2002 |
| WO | WO 02/28368 | 4/2002 |
| WO | WO 02/30394 | 4/2002 |
| WO | WO 02/34237 | 5/2002 |
| WO | WO 02/38107 | 5/2002 |
| WO | WO 02/43806 | 6/2002 |
| WO | WO 02/45682 | 6/2002 |
| WO | WO 02/49616 | 6/2002 |
| WO | WO 02/051483 | 7/2002 |
| WO | WO 02/060532 | 8/2002 |
| WO | WO 02/060533 | 8/2002 |
| WO | WO 02/060875 | 8/2002 |
| WO | WO 02/060896 | 8/2002 |
| WO | WO 02/060898 | 8/2002 |
| WO | WO 02/062317 | 8/2002 |
| WO | 02/083079 | 10/2002 |
| WO | WO 02/083079 | 10/2002 |
| WO | WO 02/083113 | 10/2002 |
| WO | WO 03/024433 | 3/2003 |
| WO | WO 03/047578 | 6/2003 |

OTHER PUBLICATIONS

Bartow et al., "An Update of its Pharmacological Properties and Therapeutic Efficacy in the Management of Asthma," Drugs, 55(2):303-322 (1998).

Becker et al. "Formoterol, a new long-acting selective b2-adrenergic receptor agonist: Double-blind comparison with salbutamol and placebo in children with asthma" J. Allergy Clin. Immunol. 84:891-895 (1989).

Campbell et al., "A comparison of the efficacy of long-acting B2-agonists:eformoterol via Turbohaler(R) and salmeterol via pressurized metered dose inhaler or Accuhaler(R), in mild to moderate asthmatics," Respiratory Medicine 93:236-244 (1999).

Campestrini et al., "Automated and sensitive method fo the determination of formoterol in human plasma by high-performance liquid chromatography and electrochemical detection," Journal of Chromatography B 704:221-229 (1997).

Cazzola et al., "Long-Acting b2-Agonists in the Treatment of Acute Exacerbations of COPD," Clin. Drug Invest. 22(6):168-174 (2002.

Daughjerg et al. "Duration of action of formoterol and salbutamol dry-powder inhalation in prevention of exercise-induced asthma in children" Acta Paediatr. 85:684-687 (1996).

Dellamary et al., "Hollow Porous Particles in Meterd Dose Inhalers," Pharmaceutical Research, 17(2):168-174 (2000).

Derwent#000971705, WPI Acc. No. 1973-48969U/197335 citing German Patent Application No. DE 2305092 A, "Alpha-aminomethylbenzyl alcohol derives.-prepd. by redn. of corresponding protected derives."

Derwent#010743444, WPI Acc No. 1996-240399/199625 for German Patent Application DE 19541689, "Medicament contg. ciclesonid and beta2-sympathomimetic for treating chronic obstructive respiratory disease".

Derwent#012030009, EPI Acc No. 1998-446919-199838 for PCT Patent Application WO 98/34595, "Pressurised liquid aerosol propellant for pharmaceutical inhalers—contains carbondioxide and hydro-fluoroalkane; give more consistent dosing and abetter particle size spectrum".

(56) References Cited

OTHER PUBLICATIONS

Derwent#013011051, WPI Acc No. 2000-182903/200016 for PCT Patent Application WO 00/06121, "Aerosol propellant comprising dinitrogen monoxide and hydrofluoroalkane and optionally containing a pharmaceutically active substance".
Derwent#013023586, WPI Acc No. 2000-195437/200017, for PCT Patent Application WO 00/07567, "Aerosol formulation of rdrug administration, containing small amount of cromoglycate or nedocromil salt as drug carrier, to improve dispersion stability and accuracy of dosing".
Derwent#013024375, WPI Acc No. 2000-196226/200018 for German Patent Application DE19835346, "Two-part drug capsule for use in powder inhalers is formed from hydrophobic plastics, preferably high density polyethylene".
Derwent#013132855, WPI Acc No. 2000-304726/200027, for German Patent De19847970, "Stable concentrated liquid formulation of inhalable drug, e.g. formoterol or salbutamol, in solution or suspensionmedium, used after dilution for treatment of respiratory disorders by inhalation".
Derwent#013227765, WPI Acc No. 2000-399639/200034, for PCT Patent Application WO 00/28979, "Use of magnesium state for stabilization of dry powder inhalation formlations to improve ersistance to moisture".
Derwent#013790372, WPI Acc No. 2001-274583/200129, for PCT Patent Application WO 01/22956, "Drug combination of soft steroid and beta-2-adrenorecetptor agonist, administered by inhalation for effective treatment of respiratory or allergic diseases, e.g. asthma".
Derwent#014808338, EPI Acc No. 2002-629044/200268, for PCT Patent Application WO 02/060533, "Medicament containing a betamimetic and an oxitropium slat useful for the treatment of respiratory disorders with reduced side effects".
Derwent#014816787, EIP Acc No. 2002-637493/200269, for PCT Patent Application Wo 02/060532, "Medicament containing a betamimetic and an ipratropium salt useful for the treatment of respiratoy disorders with reduced side effects".
Eidkelberg et al., "Ligand-independent Activation of the Glucocorticoid Receptor by b2-Adrenergic Receptor Agonists in Primary Human Lung Fibroblasts and Bascular Smooth Muscle Cells," J. Biol. Chem. 272(2):1005-1010 (1999).
Ekstrom et al., "Low-dose formoterol Turbuhaler(R) (Oxis(R)) b.i.d,, a 3-month placebo-controlled comparison with terbutaline (q.i.d.)," Respiratory Medicine 92:1040-1045 (1998).
"Flovent," Glaxo Wellcome Inc., Physicians' Desk Reference 54th Ed., (2000), pp. 1186-1389.
Farmer et al, "b-Adrenergic agonists exert their "anti-inflammatory" effects in monocytic cells through the IkB/NF-kB pathway," Am. J. Physiol. Lung. Cell. Mol. Physiol. 279:1675-682 (2000).
Greening et al., "Added salmeterol versus higher-dose corticosteroid in asthma patients with symptoms on existing inhaled corticosteroid," The Lancet 344:219-244 (1994).
Grootendorst et al., "Effect of oral prednisolone on the bronchoprotective effect of formoterol in patient with persistent asthma," Eur. Respir. J. 17:374-379 (2001).
Hardman et al. (Eds.), Goodman Gilman's The Pharmacological Basis of Therapeutics, 1996, p. 665.
Ida "Comparison of the Action of BD 40A and some Other b-Adrenoceptor Stimulants on the Isolated Trachea and Atria of the Guinea Pig" Arzneim.-Forsch, (Drug Res) 26:839-842 (1976).
Ida "Cardiorespiratory Activities of 3-Formylamino-4-hydroxy-a-(N-1-methyl-2-p-methoxyphenethylaminomethyl)benzylalcohol-hemifumarate (BD 40A) and some other b-Adrenoceptor Stimulants in Conscious Guinea Pigs" Arzneim.-Forsch, (Drug Res.) 26:1337-1340 (1976).
Ida, Hisasbi, "Pharmacology of Formoterol, (aRS)-3-formamido-4-hydroxy-a-[[[(aRS)-p-methoxy-a-methylphenethyl]amino]methyl]benzyl acohol fumatate dehydrate (BD 40A)," Oyo Yakui 21(2):201-210 (1981).

Ito et al., "Glucocorticoid Receptor Recruitment of Histone Deacetylase 2 Inhibits Interleukin-1b-Induced Histone H4 Acetylation on Lysines 8 and 12," Molecular and Cellular Biology 20(18):6892-6903 (2000).
Ito et al., "p65-activated Histone Acetyltransferase Activity is Repressed by Glucocorticoids," J. Biol. Chem. 276(32):30208-30215 (2001).
Kamimura et al. "Quantitative Determination of the b-adrenoceptor stimulant Formoterol in Urine by Gas Chromatograph Mass Sptectrometry" J. Chrom. 229:337-345 (1982).
Kaumann et al., "Direct Labelling of myocardial B1-adrenoreceptors; Comparison of Binding Affinity of 3H-(−)-bisoprolol with its blocking potency," Arch. Pharm. 331:27-39 (1985).
Korn et al., "Effects of formoteral and budesonide on GM-CSF and IL-8 secretion by triggered human bronchial epithelial cells," Eur. Respir. J. 17:1070-1077 (2001).
Lebecque et al. "Effet d'une dose unique de formoterol par voie daerosol-doseur chez l'enfant asthmatique" Rev. Mal. Resp. 11:47-50 (1994).
Lecaillon et al., "Parmacokinetics and tolerability of formoterol in healthy volunteers after a single high dose of Foradil dry powder inhalation via aerolizer (TM)," Eur. J. Clin. Pharm. 55:131-139(1999).
Leckie et al., "Novel Therpy of COPD," Expert Opin. Investig. Drugs 9(1):3-23 (2000).
Lemoine et al., "Direct labeling of B2-adrenoreceptors; Comparison of binding potency of 3H-ICI 118,551 and blocking potency of ICI 118,551," Arch. Pharm. 331:40-51 (1985).
Lipworth et al., "Effects of Treatmet with Formoterol on Bronchoprotection against Methacholine," Am. J. Med. 104:431-438 (1998).
Lofdahl et al. "Formoterol Fumarate, a new b2-adrenoceptor agonist" Allergy 44:264-271 (1989).
Lotvall et al., "Similar bronchodilation with formoterol delivered by Aerolizer or Turbuhaler," Cen. Respir. J. 6(5):412-416 (1999).
Maesen et al. "Formoterol Suspension Aerosol" Chest 102:1544-1549 (1992).
Maesen et al. "The Effect of Maximal Doses of Formoterol and Salbutamol from a Metered Dose Inhaler on Pulse Rates, ECG, and Serum Potassium Concentrations" Chest 99:1367-1373 (1991).
Maesen et al. "Formoterol as Dry Powder Inhalation" Chest 101:1376-1381 (1992).
Malolepszy et al., "Safety of formoterol Turbuhaler(TM) at cumulative dose of 90 mg in patients with acute bronchial obstruction," Eur. Respir. J. 18:928-934 (2001).
Miller et al. "Chronic Effects of the Novel Glucocorticosteroid RPR 106541 Administered to Beagle Dogs by Inhalation" Toxic. Path. 28:226-236 (2000).
Murase et al. "New b-Adrenoreceptor Stimulaints. Studies on 3-Acylarmino-4-hydroxy-a-(N-substituted aminomethyl)benzyl Alcohols" Chem Pharm. Bull. 26:1368-1377 (1977).
Nielsen et al, "Flow-dependent effect of formoterol dry powder inhaled from the Aetolizer(R)," Eur. Respir. J. 10:2105-2109 (1997).
Nightingale et al, "Differential Effect of Formoterol on Adenosine Monophophate and Histamine Reactivity in Asthma," Am. J. Respir. Crit. Care Med. 159 1786-1790 (1999).
Nogrady, T., (Editor), Medicinal Chemistyr: A Biochemical Approach, Oxford University Press, New York, pp. 388-392 (1985).
O'Connor "Combination Therapy," Pulm. Pharm. & Ther. 11:379-399 (1998).
Oddera et al., "Salmetereol Enhances the Inhibitory Activity of Dexamethasone on Allergen-Induced Blood Mononuclear Cell Activation," Respiration 65:199-204 (1998).
Package Insert for: Advair(TM) Discus http://fb.e-files.net/PackageInsert?Advair.htm (Accessed on Sep. 26, 2002) (Copyright, 1999 Glaxo Wellcome Inc.)
Palmqvist et al, "Inhaled dry-powder formoterol and almeterol in asthmatic patients: onset of action, duration of effect and potency," Eur. Respir. J. 10:2484-2489 (1997).
Palmqvist et al., "Onset of Bronchodilation of Budesonide?formoterol vs. Salmeterol/Fluticasone in Single Inhalers," Pulm. Pharm. & Ther. 14:29-34 (2001).

(56) References Cited

OTHER PUBLICATIONS

Pang et al., "Regulation of TNF-a-induced cotaxin release from cultured human airway smooth muscle cells by b2-agonists and corticoseroids," FASEB J. 15:261-269 (2001).
Pang et al., "Synergistic Inhibition by b2-Agonists and Corticosteroids on Tumor Necrosis Factor-a-Induced Interlenkin-8 Release from Cultured Human Airway Smooth-Muscle Cells," Am. J. Respir. Cell Mol. Bio. 23:79-85 (2000).
Pauwels et al., "Effect of Inhaled Formoterol and Budesonide on Exacerbations of Asthma," The New England J. Med. 337(20):1405-1411 (1947).
Physicians' Desk Reference: PDR, Orndell, J.J.: Medical Econimics Co., pp. 535-537, 480-482, 2828-2829 (2000).
Rico-Mendez et al., "Formoterol en polva seco, dos veces al dia versus salbutamol aerosol, cuatro veces al dia, en pacientes con asma eatable," Revista Alergia Mexico XLVI(5):130-135 (1999).
Ringdal et al, "Onset and duration of action of single doses of formoterol inhaled via Turbuhaler(R)," Resp. Med. 92:1017-1021 (1998).
Sasaki et al. "Desposition and metabolism of formoterol fumarate, a new bronchodilator, in rats and dogs" Xenobiotic 12:803-812 (1982).
Scheen Pharma-Clinics le Medicament du Mois le formoterol (Oxis Turbohaler) Rev. Med. Liege 53:11:715-718 (1998).
Schreurs et al, "A dose-response study with formoterol Turbuhaler(R) as maintenance therapy in asthmatic patients," Eur. Respir. J. 9:1678-1683 (1996).
Seberova et al., "Oxis(R) (formoterol given by Turbuhaler(R)) showed as rapid an onset of action as salbutamol given by a pMDI," Resp. Med. 94:607-611 (2000).
Selroos et al, "Delivery Deviceds for Inhaled Asthma Medication," Clin. Immunother. 6:273-299 (1996).
Seldon et al., "Albuterol Does Not Antagonize the Inhibitory Effect of Dexamethasone on Monocyte Cytokine Release," Am. J. Respir. Crit. Care Med. 157:803-809 (1998).
Silvestri et al., "Fluticasone and salmeterol donregulate in vitro, fibroblast proliferation and ICAM-1 or H-CAM expressions," Eru. Respir. J. 18:139-145 (2001).
Skold et al., "Glucocorticoids Augment Fibroblast-Mediated Contration of Collagen Gels by inhibition of Endogenous PGE Production," Proc. Assoc. Am. Phys. 111(3):239-258 (1999).
Smaldone et al., "Budesonide Inhalation Suspension in Chemically Compatable with Other Nebulizing Formulations," Chest 119(4)Suppl: 98S (2000).
Sovijarvi et al. "Preventive Effects of Inhaled Formoterol and Salbutamol on Histamine-Induced Bronchoconstriction—A Placebo-Controlled Study" Respiration 59:279-282 (1992).
Stevens et al. "Use of the Steroid Derivative RPR 106541 in Combination with Site-Directed Mutagenesis for Enhanced Cytochrome P-450 3A4 Structure/Funtion Analysis" J. Pharma. Exp. Ther. 290:594-602 (1999).
Stewart et al., "Acute formoeterol administration has no argogenic effect in nonasthmatic athletes," Medicine & Science in Sports & Exercise 34(2):213-217 (2002).
Tomioka et al., "Anti-Allergic Activities of the b-Adrenoreceptor Stimulant Formoterol (BD-40A)," Arch. Int. Pharmacodyn. 250 279-292 (1981).
Totterman et al., "Tolerability to high doses of formoterol and terbutaline via Turbuhaler(R) for 3 days in stable asthmatic patients," Eur. Respir. J. 12:573-579 (1998).
Ullman et al., "Formoterol inhaled as dry powder or via pressurized meterd-dose inhaler in a cumulative dose-response study," Allergy 51:745-748 (1996).
Van den Berg et al. "Evaluation of different doses of formoterol from a newly developed powder inhalation device in asthmatic patients" Fundam. Clin. Pharmacol. 9:593-603 (1995).
Vianna et al., "Bronchodilators and Corticosteroids in the Treatment of Asthma," Drugs of Today 34(3):203-223 (1998).
Wallin et al., "Time course and duration of bronchodilatation with formoterol dry powder in patients with stable asthma" Thorax 48:611-614 (1993).
Warne, "The discovery and clinical development of RPR 106541: an airway-selective steroid for the treatment of asthma," Emerging Drugs 5(2):231-239 (2000).
Wilding et al., "Effect of long term treatment with salmeterol on asthma control: a double blind randomized crossover study," British Med. J. 314:1441-1446 (1997).
Woolcock et al., "Comparison of Addition of Salmeterol to Inhaled Sterods with Doubling of the Dose of Inhaled Steroids," Am. J. Respir. Crit. Care Med. 153:1481-1488 (1996).
Yokoi et al. "The Development of a Radioimmunoassay for Formoterol" Life Sciences 33:1665-1672 (1983).
Yoshida et al., "Acute, Subacute and Chronic toxicity Studies of a Bronchodilator, Formoterol Fumarate (BD 40)" Oyo Yakuri, 26(5), 811-29 (1983).
Derwent WPI Acc No. 2000-304726 for PCT Patent Application WO 00/23037, "Stable concentrated liquid formulation of inhalable drug, e.g. formoterol or salbutamol, in solution or suspension medium, used after dilution for treatment of respiratory disorders by inhalation".
Bedi "Inhaled Corticosteroids in COPD" Indian J Chest Allied Sci 2005; 47: 243-244.
Nials, A.T., et al., "Effects of β-adrenoceptor agonists in human bronchial smooth muscle", Br. J. Pharmacol., 193, 110: 112-1116.
Nials, A.T., et al., "Formoterol on airway smooth muscle and human lung mast cells . . . ", European Journal of Pharmacology, 1994, 251: 127-135.
Mohammed, S.P. et al., "Duration of action of inhaled vs. Intravenous β2-adrenoceptor . . . ", Pulmonary Pharmacology & Theraeutics, 2000, 13:287-292.
Dey v. Sepracor; 1:07-cv-2353; Complaint.
Dey v. Sepracor; 1:07-cv-2353; Answer and Counterclaims.
Dey v. Sepracor; 1:07-cv-2353; Reply to Counterclaims.
Dey v. Sepracor; 1:07-cv-2353; Answer to Additional Claims.
Dey v. Sepracor; 1:07-cv-2353; Discovery Plan.
Lachman et al., "Chapter 26: Kinetic Principles and Stability Testing", The Theory and Practice of Industrial Pharmacy, 1986, 3rd Edition.
Whelan, et al., "Comparison of the Anti-Inflammatory Properties of Formoterol, Salbutamol, and Salmeterol in Guinea-Pig Skin and Lung", British Journal of Pharmacology, 1993, pp. 613-618, 110.
Remington, "Chapter 38: Stability of Pharmaceutical Products", The Science and Practice of Pharmacology, 1995, 1995, p. 639, 19th Edition.
Rosenborg, et al., "Mass Balance and Metabolism of [(3)H]Formoterol in Healthy Men after Combined i.v. and Oral Administration-Mimicking Inhalation", Drug Metabolism and Disposition, 1999, pp. 1104-1116, 27(10).
Puigbo, et al., "A New Therapeutical Alternative in the Management of Acute Asthma (Preliminary Report)", Alergia, Asma e Inmunologia, 2000, pp. 73-76, II(2).
Maesen, et al., "Formoterol Suspension Aerosol. Comparison with Formoterol Solution Aerosol for 12 Weeks in Asthmatic Patients", Chest, 1992, pp. 1544-1549, 102.
U.S. Appl. No. 13/052,792: Non-Final Office Action dated Feb. 28, 2013. Please note that this serial number is associated with the parent application of this present application.

* cited by examiner

FORMOTEROL/STEROID BRONCHODILATING COMPOSITIONS AND METHODS OF USE THEREOF

This patent application is a continuation of U.S. patent application Ser. No. 10/145,978, filed May 13, 2002, which is a divisional application of U.S. application Ser. No. 09/887,496, to Banerjee et al., entitled "FORMOTEROL/STEROID BRONCHODILATING COMPOSITIONS AND METHODS OF USE THEREOF," filed Jun. 22, 2001. Benefit of priority under 35 U.S.C. §119(e) is also claimed to U.S. provisional patent application Ser. No. 60/284,607, filed Apr. 17, 2001, to Banerjee et al. The disclosures of the above-referenced applications are incorporated herein by reference in their entirety.

RELATED APPLICATIONS

This application is a divisional application of U.S. application Ser. No. 09/887,496, to Banerjee et al., entitled "FORMOTEROL/STEROID BRONCHODILATING COMPOSITIONS AND METHODS OF USE THEREOF," filed Jun. 22, 2001. Benefit of priority under 35 U.S.C. §119(e) is also claimed to U.S. provisional patent application Ser. No. 60/284,607, filed Apr. 17, 2001, to Banerjee et al. The disclosures of the above-referenced applications are incorporated herein by reference in their entirety.

FIELD OF THE INVENTION

Compositions and methods are provided relating to treatment, prevention, or amelioration of one or more symptoms of bronchoconstrictive disorders. In particular, the compositions and methods herein include formoterol, and/or a derivative thereof, and a steroid, and/or a derivative thereof. The compositions are propellant-free, sterile unit dose or multi-dose inhalation solutions intended for administration via nebulization.

BACKGROUND OF THE INVENTION

Bronchoconstrictive disorders affect millions worldwide. Such disorders include asthma (including bronchial asthma, allergic asthma and intrinsic asthma, e.g., late asthma and airway hyper-responsiveness), chronic bronchitis and other chronic obstructive pulmonary diseases. Compounds having $\beta_2$-adrenoreceptor agonist activity have been developed to treat these conditions. Such compounds include, but are not limited to, Albuterol ($\alpha^1$-(((1,1-dimethylethyl)amino)methyl)-4-hydroxy-1,3-benzenedimethanol); Bambuterol (dimethylcarbamic acid 5-(2-((1,1-dimethylethyl)amino)-1-hydroxyethyl)-1,3-phenylene ester); Bitolterol (4-methylbenzoic acid 4-(2-(((1,1-dimethylethyl)amino)-1-hydroxyethyl)-1,2-phenylene ester); Broxaterol (3-bromo-α-(((1,1-dimethylethyl)amino)methyl)-5-isoxazolemethanol); Isoproterenol (4-(1-hydroxy-2-((1-methylethyl)amino)ethyl)-1,2-benzenediol); Trimetoquinol (1,2,3,4-tetrahydro-1-((3,4,5-trimethoxyphenyl)methyl)-6,7-isoquinolinediol); Clenbuterol (4-amino-3,5-dichloro-α-(((1,1-dimethylethyl)amino)methyl)benzenemethanol); Fenoterol (5-(1-hydroxy-2-((2-(4-hydroxyphenyl)-1-methylethyl)amino)ethyl)-1,3-benzenediol); Formoterol (2-hydroxy-5-((1RS)-1-hydroxy-2-(((1RS)-2-(p-methoxyphenyl)-1-methylethyl)amino)ethyl)formanilide); (R,R)-Formoterol; Desformoterol ((R,R) or (S,S)-3-amino-4-hydroxy-α-(((2-(4-methoxyphenyl)-1-methylethyl)amino)methyl)benzenemethanol); Hexoprenaline (4,4'-(1,6-hexanediyl)-bis(imino(1-hydroxy-2,1-ethanediyl)))bis-1,2-benzenediol); Isoetharine (4-(1-hydroxy-2-((1-methylethyl)amino)butyl)-1,2-benzenediol); Isoprenaline (4-(1-hydroxy-2-((1-methylethyl)amino)ethyl)-1,2-benzenediol); Metaproterenol (5-(1-hydroxy-2-((1-methylethyl)amino)ethyl)-1,3-benzenediol); Picumeterol (4-amino-3,5-dichloro-α-(((6-(2-(2-pyridinyl)ethoxy)hexyl)amino)methyl)benzenemethanol); Pirbuterol ($\alpha^6$-(((1,1-dimethylethyl)amino)methyl)-3-hydroxy-2,6-pyridinemethanol); Procaterol ((($R^*,S^*$)-(±)-8-hydroxy-5-(1-hydroxy-2-((1-methylethyl)amino)butyl)-2(1H)-quinolinone); Reproterol ((7-(3-((2-(3,5-dihydroxyphenyl)-2-hydroxyethyl)amino)propyl)-3,7-dihydro-1,3-dimethyl-1H-purine-2,6-dione); Rimiterol (4-(hydroxy-2-piperidinylmethyl)-1,2-benzenediol); Salbutamol ((±)-$\alpha^1$-(((1,1-dimethylethyl)amino)methyl)-4-hydroxy-1,3-benzenedimethanol); (R)-Salbutamol; Salmeterol ((±)-4-hydroxy-$\alpha^1$-(((6-(4-phenylbutoxy)hexyl)amino)methyl)-1,3-benzenedimethanol); (R)-Salmeterol; Terbutaline (5-(2-((1,1-dimethylethyl)amino)-1-hydroxyethyl)-1,3-benzenediol); Tulobuterol (2-chloro-α-(((1,1-dimethylethyl)amino)methyl)benzenemethanol); and TA-2005 (8-hydroxy-5-((1R)-1-hydroxy-2-(N-((1R)-2-(4-methoxyphenyl)-1-methylethyl)amino)ethyl)carbostyril hydrochloride).

These compounds are typically formulated for inhalation therapy. Aqueous or liquid formulations are preferred over formulations of solids. Powdered formulations are more difficult to administer, particularly to the young and elderly who are most often the patients in need of such therapy. Compounds, such as formoterol, which has many desirable properties, are not adequately stable in aqueous solutions to be formulated as liquids. Hence there is a need for formulations of compounds, such as formoterol, in a form that can be conveniently administered.

Other prophylactic therapeutics for use in treatment of bronchoconstrictive disorders include steroidal anti-inflammatory agents such as beclomethasone dipropionate (BDP), beclomethasone monopropionate (BMP), flunisolide, triamcenolone acetonide, dexamethasone, tipredane, ciclesonid, mometasone, mometasone furoate (Asmanex® Twisthaler™, Shering-Plough Corporation, Kenilworth, N.J.), RPR 106541, having the formula

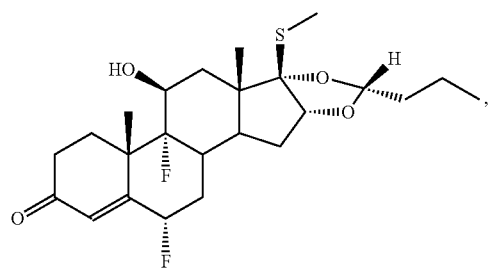

fluticasone, fluticasone propionate and budesonide. These agents can be formulated for inhalation therapy.

Effective treatment of asthma and other bronchoconstrictive disorders often requires combination therapy. It is advantageous to administer combinations of bronchodilators and other agents, such as anti-steroidal agents. Since some the $\beta_2$-adrenoreceptor agonist compounds are not available as aqueous or liquid formulations, combinations thereof with other agents, are not available as aqueous or liquid formulations. Since aqueous or liquid formulations are preferred, there is need to develop liquid formulations. Therefore, it is an object herein to provide stable liquid formulations of β$_2$-adrenoreceptor agonist compounds. It is a further object herein to improve the stability of existing liquid formulations.

SUMMARY OF THE INVENTION

Compositions and methods for treatment, prevention, or amelioration of one or more symptoms of bronchoconstrictive disorders are provided. The compositions provided herein are stable solutions of a bronchodilating agent, and/or a derivative thereof, and a prophylactic therapeutic agent, including, but not limited to, a steroid and/or a derivative thereof. The compositions are formulated in a pharmacologically suitable fluid that contains water and that are stable during long term storage. The compositions are suitable for direct administration to a subject in need thereof. Pharmacologically suitable fluids include, but are not limited to, polar fluids, including protic fluids. In certain embodiments herein, the compositions are aqueous solutions.

Compositions provided herein possess an estimated shelf-life of greater than 1, 2 or 3 months usage time at 25° C. and greater than or equal to 1, 2 or 3 years storage time at 5° C. In certain of these embodiments, using Arrhenius kinetics, >80% or >85% or >90% or >95% estimated bronchodilating agent remains after such storage. These compositions are particularly useful for administration via nebulization. In certain embodiments herein, the subject is a mammal. In other embodiments, the subject is a human.

The compositions provided herein are formulated to remain stable over a relatively long period of time. For example, the compositions provided herein are stored between −15° C. and 25° C., or between 2° C. and 8° C. In one embodiment, the compositions are stored at 5° C.

Among the bronchodilating agents for use herein are Albuterol (((1,1-dimethylethyl)amino)methyl)-4-hydroxy-1,3-benzenedimethanol); Bambuterol (dimethylcarbamic acid 5-(2-((1,1-dimethylethyl)amino)-1-hydroxyethyl)-1,3-phenylene ester); Bitolterol (4-methylbenzoic acid 4-(2-((1,1-dimethylethyl)amino)-1-hydroxyethyl)-1,2-phenylene ester); Broxaterol (3-bromo-α-(((1,1-dimethylethyl)amino) methyl)-5-isoxazolemethanol); Isoproterenol (4-(1-hydroxy-2-((1-methylethyl)amino)ethyl)-1,2-benzenediol); Trimetoquinol (1,2,3,4-tetrahydro-1-((3,4,5-trimethoxyphenyl) methyl)-6,7-isoquinolinediol); Clenbuterol (4-amino-3,5-dichloro-α-(((1,1-dimethylethyl)amino)methyl) benzenemethanol); Fenoterol (5-(1-hydroxy-2-((2-(4-hydroxyphenyl)-1-methylethyl)amino)ethyl)-1,3-benzenediol); Formoterol (2-hydroxy-5-((1RS)-1-hydroxy-2-(((1RS)-2-(p-methoxyphenyl)-1-methylethyl)amino) ethyl)formanilide); (R,R)-Formoterol; Desformoterol ((R,R) or (S,S)-3-amino-4-hydroxy-α-(((2-(4-methoxyphenyl)-1-methylethyl)amino)methyl)benzenemethanol); Hexoprenaline (4,4'-(1,6-hexanediyl)-bis(imino(1-hydroxy-2,1-ethanediyl)))bis-1,2-benzenediol); Isoetharine (4-(1-hydroxy-2-((1-methylethyl)amino)butyl)-1,2-benzenediol); Isoprenaline (4-(1-hydroxy-2-((1-methylethyl)amino) ethyl)-1,2-benzenediol); Metaproterenol (5-(1-hydroxy-2-((1-methylethyl)amino)ethyl)-1,3-benzenediol); Picumeterol (4-amino-3,5-dichloro-α-(((6-(2-(2-pyridinyl)ethoxy) hexyl)amino)methyl)benzenemethanol); Pirbuterol (α$^6$-(((1,1-dimethylethyl)amino)methyl)-3-hydroxy-2,6-pyridinemethanol); Procaterol (((R*,S*)-(±)-8-hydroxy-5-(1-hydroxy-2-((1-methylethyl)amino)butyl)-2(1H)-quinolinone); Reproterol ((7-(3-((2-(3,5-dihydroxyphenyl)-2-hydroxyethyl)amino)propyl)-3,7-dihydro-1,3-dimethyl-1H-purine-2,6-dione); Rimiterol (4-(hydroxy-2-piperidinylmethyl)-1,2-benzenediol); Salbutamol ((±)-α$^1$-(((1,1-dimethylethyl)amino)methyl)-4-hydroxy-1,3-benzenedimethanol); (R)-Salbutamol; Salmeterol ((±)-4-hydroxy-α$^1$-(((6-(4-phenylbutoxy)hexyl)amino)methyl)-1,3-benzenedimethanol); (R)-Salmeterol; Terbutaline (5-(2-((1,1-dimethylethyl)amino)-1-hydroxyethyl)-1,3-benzenediol); Tulobuterol (2-chloro-α-(((1,1-dimethylethyl) amino)methyl)benzenemethanol); and TA-2005 (8-hydroxy-5-((1R)-1-hydroxy-2-(N-((1R)-2-(4-methoxyphenyl)-1-methylethyl)amino)ethyl)carbostyril hydrochloride).

Of particular interest herein is formoterol, having the formula:

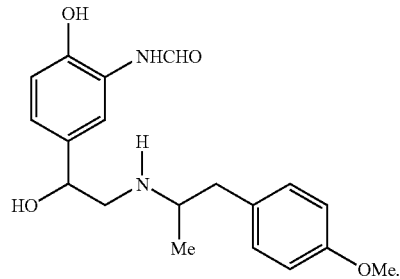

Formoterol for use in the compositions and methods provided herein includes 2-hydroxy-5-((1RS)-1-hydroxy-2-(((1RS)-2-(p-methoxyphenyl)-1-methylethyl)amino)ethyl) formanilide; or a stereoisomer thereof; and also includes the single enantiomers 2-hydroxy-5-((1S)-1-hydroxy-2-(((1S)-2-(p-methoxyphenyl)-1-methylethyl)amino)ethyl)formanilide and 2-hydroxy-5-((1R)-1-hydroxy-2-(((1R)-2-(p-methoxyphenyl)-1-methylethyl)amino)ethyl)formanilide.

Prophylactic therapeutics for use in the compositions and methods herein include steroidal anti-inflammatory agents, including, but not limited to, beclomethasone dipropionate (BDP), beclomethasone monopropionate (BMP), flunisolide, triamcinolone acetonide, dexamethasone, tipredane, ciclesonid, rofleponide, mometasone, mometasone furoate (Asmanex® Twisthaler™, Shering-Plough Corporation, Kenilworth, N.J.), RPR 106541, fluticasone or fluticasone propionate and budesonide, or derivatives thereof. In one embodiment, the steroidal anti-inflammatory is fluticasone, fluticasone propionate, budesonide, or a derivative thereof.

In certain embodiments, the compositions are administered via nebulization. Administration of a nebulized aerosol is preferred over the use of dry powders for inhalation in certain subject populations, including pediatric and geriatric groups.

In one embodiment, the compositions for use in the methods provided herein contain a pharmaceutically acceptable derivative of formoterol. In another embodiment, the compositions for use in the methods provided herein contain a pharmaceutically acceptable salt of formoterol. Pharmaceutically acceptable salts include, but are not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. In one embodiment, the compositions for use in the methods provided herein contain formoterol fumarate or formoterol fumarate dihydrate. In another embodiment, the compositions for use in the methods provided herein contain formoterol tartrate.

In another embodiment, the compositions for use in the methods provided herein contain budesonide or fluticasone propionate. Compositions containing formoterol, budesonide and a fluoroalkane propellant are disclosed in U.S. Pat. No. 6,004,537. Compositions containing formoterol and budesonide for dry powder inhalation or metered dose inhalation are disclosed in U.S. Pat. Nos. 5,674,860 and 5,972,919. These references do not disclose the compositions provided herein that are formulated in a pharmacologically suitable fluid, as defined herein, that contains water and that are stable during long term storage.

Also provided herein are combinations containing compositions provided herein. The compositions may be formulated separately or mixed in a single composition. The compositions contained in the combinations may be administered sequentially or intermittently. The compositions contained in the combinations can be mixed prior to use or can be formulated as a single composition. The combinations may further include a nebulizer. The combinations can be packaged as kits, which optionally contain other components, including instructions for use of the nebulizer and/or instructions for mixing the compositions if provided separately.

Any nebulizer is contemplated for use in the kits and methods provided herein. In particular, the nebulizers for use herein nebulize liquid formulations, including the compositions provided herein, containing no propellant. The nebulizer may produce the nebulized mist by any method known to those of skill in the art, including, but not limited to, compressed air, ultrasonic waves, or vibration. The nebulizer may further have an internal baffle. The internal baffle, together with the housing of the nebulizer, selectively removes large droplets from the mist by impaction and allows the droplets to return to the reservoir. The fine aerosol droplets thus produced are entrained into the lung by the inhaling air/oxygen.

Methods for the treatment, prevention, or amelioration of one or more symptoms of bronchoconstrictive disorders, including, but not limited to, asthma, including, but not limited to, bronchial asthma, allergic asthma and intrinsic asthma, e.g., late asthma and airway hyper-responsiveness; chronic bronchitis; and other chronic obstructive pulmonary diseases are provided. The methods involve administering an effective amount of a pharmaceutical composition provided herein to a subject in need of such treatment.

Articles of manufacture, containing packaging material, a composition provided herein, which is useful for treatment, prevention or amelioration of one or more symptoms of diseases or disorders associated with undesired and/or uncontrolled bronchoconstriction, and a label that indicates that the composition is used for treatment, prevention or amelioration of one or more symptoms of diseases or disorders associated with undesired and/or uncontrolled bronchoconstriction, are also provided.

DETAILED DESCRIPTION OF PREFERRED EMBODIMENTS

Definitions

Unless defined otherwise, all technical and scientific terms used herein have the same meaning as is commonly understood by one of ordinary skill in the art to which this invention belongs. All patents, applications, published applications and other publications are incorporated by reference in their entirety. In the event that there are a plurality of definitions for a term herein, those in this section prevail unless stated otherwise.

As used herein, formoterol refers to 2-hydroxy-5-((1RS)-1-hydroxy-2-(((1RS)-2-(p-methoxyphenyl)-1-methylethyl)amino)ethyl)formanilide; or a stereoisomer thereof. The term formoterol also refers to the single enantiomers 2-hydroxy-5-((1S)-1-hydroxy-2-(1S)-2-(p-methoxyphenyl)-1-methyl-ethyl)amino)ethyl)formanilide and 2-hydroxy-5-((1R)-1-hydroxy-2-(((1R)-2-(p-methoxyphenyl)-1-methylethyl)amino)ethyl)formanilide.

As used herein, formoterol fumarate refers to a salt of formoterol having the formula (formoterol)*½ fumarate. Formoterol fumarate dihydrate refers to the dihydrate of formoterol fumarate.

As used herein, formoterol free base refers to the neutral, anhydrous form of formoterol. Thus, a recitation that a composition contains, e.g., 59 µg/mL of formoterol free base means that the composition contains 59 µg/mL of neutral, anhydrous formoterol. Such compositions may be prepared using a derivative of formoterol.

As used herein, budesonide refers to (RS)-11β,16α,17,21-tetrahydroxypregna-1,4-diene-3,20-dione cyclic 16,17-acetal with butraldehyde. The term budesonide refers to the (R) isomer, the (S) isomer, and mixtures thereof.

As used herein, fluticasone refers to (6α,9α,11β,16α,17α)-6,9-difluoro-11-hydroxy-16-methyl-3-oxo-17-hydroxyandrosta-1,4-diene-17-carbothioic acid, S-fluoromethyl ester. Fluticasone propionate refers to (6α,9α,11β,16α,17α)-6,9-difluoro-11-hydroxy-16-methyl-3-oxo-17-(1-oxopropoxy)androsta-1,4-diene-17-carbothioic acid, S-fluoromethyl ester.

As used herein, an aerosol is liquid or particulate matter dispersed in air. Aerosols include dispersions of liquids, including aqueous and other solutions, and solids, including powders, in air.

As used herein, a nebulized solution refers to a solution that is dispersed in air to form an aerosol. Thus, a nebulized solution is a particular form of an aerosol.

As used herein, a nebulizer is an instrument that is capable of generating very fine liquid droplets for inhalation into the lung. Within this instrument, the nebulizing liquid or solution is atomized into a mist of droplets with a broad size distribution by methods known to those of skill in the art, including, but not limited to, compressed air, ultrasonic waves, or a vibrating orifice. Nebulizers may further contain, e.g., a baffle which, along with the housing of the instrument, selectively removes large droplets from the mist by impaction. Thus, the mist inhaled into the lung contains fine aerosol droplets.

As used herein, a pharmacologically suitable fluid is a solvent suitable for pharmaceutical use which is not a liquified propellant gas. Exemplary pharmacologically suitable fluids include polar fluids, including protic fluids such as water.

As used herein, a combination refers to any association between two or among more items.

As used herein, fluid refers to any composition that can flow. Fluids thus encompass compositions that are in the form of semi-solids, pastes, solutions, aqueous mixtures, gels, lotions, creams and other such compositions.

As used herein, a mixture is a mutual incorporation of two or more substances, without chemical union, the physical characteristics of each of the components being retained.

As used herein, the stability of a composition provided herein refers to the length of time at a given temperature that greater than 80%, 85%, 90% or 95% of the initial amount of active ingredient, e.g., formoterol, is present in the composition. Thus, for example, a composition that is stable for 30 days at 25° C. would have greater than 80%, 85%, 90% or 95% of the initial amount of active ingredient present in the composition at 30 days following storage at 25° C.

As used herein, pharmaceutically acceptable derivatives of a compound include salts, esters, enol ethers, enol esters, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl and heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl and heterocyclyl. Pharmaceutically acceptable solvates and hydrates are complexes of a compound with one or more solvent or water molecule, preferably 1 to about 100, more preferably 1 to about 10, most preferably one to about 2, 3 or 4, solvent or water molecules. Formoterol salts and hydrates are used in certain embodiments herein.

As used herein, treatment means any manner in which one or more of the symptoms of a condition, disorder or disease are ameliorated or otherwise beneficially altered. Treatment also encompasses any pharmaceutical use of the compositions herein, such as use for treating cancer.

As used herein, amelioration of the symptoms of a particular disorder by administration of a particular pharmaceutical composition refers to any lessening, whether permanent or temporary, lasting or transient that can be attributed to or associated with administration of the composition.

As used herein, a prodrug is a compound that, upon in vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388-392).

It is to be understood that the compounds for use in the compositions and methods provided herein may contain chiral centers. Such chiral centers may be of either the (R) or (S) configuration, or may be a mixture thereof. Thus, the compounds for use in the compositions provided herein may be enantiomerically pure, or be stereoisomeric or diastereomeric mixtures. It is to be understood that the chiral centers of the compounds provided herein may undergo epimerization in vivo. Thus, one of skill in the art will recognize that administration of a compound in its (R) form is equivalent, for compounds that undergo epimerization in vivo, to administration of the compound in its (S) form.

As used herein, bronchoconstriction refers to a reduction in the caliber of a bronchus or bronchi.

As used herein, undesired and/or uncontrolled bronchoconstriction refers to bronchoconstriction that results in or from a pathological symptom or condition. Pathological conditions include, but are not limited to, asthma and chronic obstructive pulmonary disease (COPD). Pathological symptoms include, but are not limited to, asthma and COPD.

As used herein, the statement that a composition is stable during "long term storage" means that the composition is suitable for administration to a subject in need thereof when it has an estimated shelf-life of greater than 1, 2 or 3 months usage time at 25° C. and greater than or equal to 1, 2 or 3 years storage time at 5° C. In certain embodiments herein, using Arrhenius kinetics, >80% or >85% or >90% or >95% estimated bronchodilating agent remains after such storage.

A. Formoterol, Budesonide and Fluticasone Propionate

1. Formoterol

Formoterol (2-hydroxy-5-(((1RS)-1-hydroxy-2-(((1RS)-2-(p-methoxyphenyl)-1-methylethyl)amino)ethyl)formanilide) is derived from adrenaline and, as noted above, is used as a $\beta_2$-stimulator in inhalation therapy of respiratory diseases, particularly for the treatment of bronchial asthma. It has been reported that in patients with reversible obstructive respiratory diseases, formoterol has a bronchodilatory effect. This effect has a relatively rapid onset (approximately 1-3 minutes) and a relatively long duration (greater than 12 hours). Formoterol inhibits the release of leukotrienes and other messenger substances involved with inflammation, such as histamines. In addition, formoterol may bring about a hyperglycemic activity.

To date, formoterol has been formulated as a dry powder and administered via devices such as the Turbuhaler® and the Aerolizer®. See, e.g., Seberova et al. (2000) *Respir. Med.* 94(6):607-611; Lotvall et al., (1999) *Can. Respir. J.* 6(51:412-416; Campbell et al. (1999) *Respir. Med.* 93(4):236-244; Nightingale et al., (1999) *Am. J. Respir. Crit. Care Med.* 159(61:1786-1790; Lecaillon et al. (1999) *Eur. J. Clin. Pharmacol.* 55(21:131-138; Bartow et al. (1998) *Drugs* 55(21:303-322; Ekstrom et al. (1998) *Respir. Med.* 92(8):1040-1045; Ringdal et al. (1998) *Respir. Med.* 92(81:1017-1021; Totterman et al. (1998) *Eur. Respir. J.* 12(31:573-579; Palmqvist et al. (1997) *Eur. Respir. J.* 10(111:2484-2489; Nielsen (1997) *Eur. Respir. J.* 10(91:2105-2109; Ullman et al. (1996) *Allergy* 51(101:745-748; Selroos et al. (1996) *Clin. Immunother.* 6:273-299; and Schreurs et al. (1996) *Eur. Respir. J.* 9(81:1678-1683.

Formoterol is also available as a tablet and a dry syrup in certain areas of the world (e.g., Atock®, marketed by Yamanouchi Pharmaceutical Co. Ltd., Japan). Formoterol formulations are also available in other areas (e.g., Europe and U.S.) for propellant-based metered dose inhalers and dry powder inhalers (e.g., Turbuhaler®, Aerolizer® and Foradil Aerolizer®). None of these formulations are water based. Sterile, stable, aqueous based inhalation solutions of formoterol for nebulization are not available, nor have they been reported.

Compositions containing formoterol in combination with other active ingredients have been disclosed. See, e.g., U.S. Pat. Nos. 5,668,110, 5,683,983, 5,677,280 and 5,654,276 (formoterol and IL-5 inhibitors), U.S. Pat. No. 6,136,603 (formoterol and antisense modulators of IL-5), U.S. Pat. No. 5,602,110 (formoterol and milrinone), U.S. Pat. No. 5,525,623 (formoterol and a tryptase inhibitor), U.S. Pat. Nos. 5,691,336, 5,877,191, 5,929,094, 5,750,549 and 5,780,467 (formoterol and a tachykinin receptor antagonist); and International Patent Application Publication Nos. WO 99/00134 (formoterol and rofleponide) and WO 99/36095 (formoterol and a dopamine $D_2$ receptor agonist).

Other compositions containing formoterol have been disclosed in U.S. Pat. Nos. 5,677,809, 6,126,919, 5,733,526, 6,071,971, 6,068,833, 5,795,564, 6,040,344, 6,041,777, 5,874,481, 5,965,622 and 6,161,536.

U.S. Pat. No. 6,150,418 discloses a "liquid active substance concentrate" containing formoterol in the form of its free base or in the form of one of the pharmacologically acceptable salts or addition products (adducts) thereof as active substance. This "liquid active substance concentrate" is reported to be a concentrated (i.e., greater than 10 mg/mL, preferably 75 to 500 mg/mL) solution or suspension that is stable for a period of several months possibly up to several years without any deterioration in the pharmaceutical quality. This patent teaches that it is the high concentration that allows for the stability of the concentrate. The "liquid active substance concentrate" is not suitable for direct administration to a subject.

U.S. Pat. No. 6,040,344 discloses an aqueous aerosol formulation of formoterol tartrate for use in a nebulizer. This patent states that the formulation disclosed therein is not attractive for long term storage.

2. Budenoside and Fluticasone Propionate

Budesonide, (RS)-11β,16α,17,21-tetrahydroxypregna-1,4-diene-3,20-dione cyclic 16,17-acetal with butraldehyde, is an anti-inflammatory, synthetic corticosteroid. Fluticasone propionate, (6α,11β,16α,17α)-6,9,-difluoro-11-hydroxy-16-methyl-3-oxo-17-(1-oxopropoxy)androsta-1,4-diene-17-carbothioic acid, S-fluoromethyl ester, is a synthetic fluorinated corticosteroid, and is known for topical dermatologic use. Topical corticosteroids constitute a class of primarily synthetic steroids used as anti-inflammatory and antipruritic agents. The mechanism of the anti-inflammatory activity of topical steroids, in general, is unclear. However, corticosteroids are thought to act by the induction of phospholipase A2 inhibitory proteins (lipocortins). It is postulated that these proteins control the biosynthesis of prostaglandins and leukotrienes by inhibiting the release of arachidonic acid.

B. Compositions for Use in Treatment, Prevention, or Amelioration of One or More Symptoms of Bronchoconstrictive Disorders Pharmaceutical compositions containing a $\beta_2$-adrenoreceptor agonist and a steroid for administration via nebulization are provided. The compositions are sterile filtered and filled in vials, including unit dose vials providing sterile unit dose formulations which are used in a nebulizer and suitably nebulized. Each unit dose vial is sterile and is suitably nebulized without contaminating other vials or the next dose. The bulk sterile formulation is sterilized by steam, gamma radiation or is prepared using sterile steroidal powder.

The unit dose vials are formed in a form-fill-seal machine or by any other suitable method known to those of skill in the art. The vials may be made of plastic materials that are suitably used in these processes. For example, plastic materials for preparing the unit dose vials include, but are not limited to, low density polyethylene, high density polyethylene, polypropylene and polyesters. In one embodiment, the plastic material is low density polyethylene.

In one embodiment, the $\beta_2$-adrenoreceptor agonist is formoterol, or a pharmaceutically acceptable derivative thereof. In other embodiments, the formoterol for use in the compositions provided herein is formoterol fumarate. Formoterol refers to 2-hydroxy-5-((1RS)-1-hydroxy-1-2-(((1RS)-2-(p-methoxyphenyl)-1-methylethyl)amino)ethyl)formanilide; or a stereo-isomer thereof. The term formoterol also refers herein to the single enantiomers 2-hydroxy-5-((1S)-1-hydroxy-2-((((1S)-2-(p-methoxypheny-1)-1-methyl ethyl)amino)ethyl)formanilide and 2-hydroxy-5-((1R)-1-hydroxy-2-(((1R)-2-(p-methoxyphenyl)-1-methylethyl)amino)ethyl) formanilide.

In one embodiment, the compositions contain, in addition to a steroidal anti-inflammatory agent, including, but not limited to, budesonide and fluticasone propionate, formoterol free base at a concentration of about 5 µg/mL to about 2 mg/mL. In other embodiments, the maximum concentration of formoterol free base in the compositions is 1.5 mg/mL. In further embodiments, the concentration of formoterol free base in the compositions is about 10 µg/mL to about 1 mg/mL, or about 50 µg/mL to about 200 µg/mL. In other embodiments, the compositions contain formoterol fumarate at a concentration of about 80 µg/mL up to about 175 to 200 µg/mL. In further embodiments, the compositions contain formoterol fumarate at a concentration of about 90 µg/mL up to about 125 to 150 µg/mL. The formoterol fumarate is formulated, in certain compositions provided herein, at a concentration of about 100 µg/mL. The formoterol fumarate is formulated, in other compositions provided herein, at a concentration of about 85 µg/mL or about 170 µg/mL. In one embodiment, the formoterol fumarate is formulated for single dosage administration via nebulization at a concentration of about 100 µg/mL. In another embodiment, the compositions contain formoterol free base at a concentration of about 40 to about 150 µg/mL, particularly about 59 or about 118 µg/mL.

The compositions provided herein further contain, in addition to a $\beta_2$-adrenoreceptor agonist, including formoterol, a steroidal anti-inflammatory agent, including, but not limited to, budesonide or fluticasone propionate. Budesonide is (RS)-11β,16α,17,21-tetrahydroxypregna-1,4-diene-3,20-dione cyclic 16,17-acetal with butraldehyde. Budesonide also refers to the (R) isomer, the (S) isomer, and mixtures thereof. Fluticasone propionate refers to (6α,11β,16α,17α)-6,9-difluoro-11-hydroxy-16-methyl-1-3-oxo-17-(1-oxopropoxy) androsta-1,4-diene-17-carbothioic acid, S-fluoromethyl ester.

In one embodiment, the compositions contain budesonide or fluticasone propionate at a concentration of about 5 µg/mL to about 2 mg/mL. In another embodiment, the compositions contain budesonide at a concentration of about 75 µg/mL to about 500 µg/mL, or about 125 µg/mL to about 500 µg/mL. In certain embodiments, the compositions contain budesonide at a concentration of about 125 µg/mL or 250 µg/mL. In another embodiment, the compositions contain fluticasone propionate at a concentration of about 75 µg/mL to about 1000 µg/mL, or about 250 µg/mL to about 1000 µg/mL. In further embodiments, the compositions contain fluticasone propionate at a concentration of about 125 µg/mL or about 250 µg/mL.

The compositions are formulated as solutions or suspensions with a pharmacologically suitable fluid. Pharmacologically suitable fluids include, but are not limited to, polar solvents, including, but not limited to, compounds that contain hydroxyl groups or other polar groups. Such solvents include, but are not limited to, water or alcohols, such as ethanol, isopropanol, and glycols including propylene glycol, polyethylene glycol, polypropylene glycol, glycol ether, glycerol and polyoxyethylene alcohols.

Polar solvents also include protic solvents, including, but not limited to, water, aqueous saline solutions with one or more pharmaceutically acceptable salt(s), alcohols, glycols or a mixture thereof. For a saline solution as the solvent or as a component thereof, particularly suitable salts are those which display no or only negligible pharmacological activity after administration.

In the embodiments herein, the compositions have a pH of about 2.0 to about 8.0. The particular pH of a given composition for long term storage provided herein may be determined empirically using standard stability assays well known to those of skill in the art (see, e.g., the Examples). For example, in certain embodiments, the compositions have a pH of about 4.0 to about 6.0, or about 4.5 to about 5.5. In certain of the above embodiments, the compositions are formulated at a pH of about 4, 4.4 or 4.6 up to about 5.5, 5.7 or 6. In other embodiments, the pH is about 5.0. It has been found herein that the rate constant for decomposition of an aqueous solution of formoterol is dependent on pH. The rate constant ($k_{obs}$) at 60° C. at a pH of 3, 4, 5 and 7 is approximately 0.62, 0.11, 0.044 and 0.55 $day^{-1}$, respectively. Therefore, the decomposition of formoterol in aqueous solution at 60° C. at a buffer concentration of 5 mM and an ionic strength of 0.05 is slowest at a pH of about 5.0.

The solubility of formoterol in aqueous solution has been found herein to be dependent on pH. Thus, at a pH of between about 5 and about 7, the aqueous solubility of formoterol at ambient temperature is approximately 2.2 mg/mL. At a pH of about 4, the aqueous solubility of formoterol at ambient temperature is approximately 3 mg/mL, while at a pH of about 3, the aqueous solubility of formoterol at ambient temperature is about 4.8 mg/mL. The solubility of formoterol in pure water, for example, high performance liquid chromatography (HPLC) water, at ambient temperature is approximately 2 mg/mL.

In other of the above embodiments, the compositions further contain a buffer, including, but not limited to, citric acid/phosphate, acetate, barbital, borate, Britton-Robinson, cacodylate, citrate, collidine, formate, maleate, Mcilvaine, phosphate, Prideaux-Ward, succinate, citrate-phosphate-borate (Teorell-Stanhagen), veronal acetate, MES (2-(N-morpholino)ethanesulfonic acid), BIS-TRIS (bis(2-hydroxyethyl)imino-tris-(hydroxymethyl)methane), ADA (N-(2-acetamido)-2-iminodiacetic acid), ACES (N-(carbamoylmethyl)-2-aminoethanesulfonaic acid), PIPES (piperazine-N,N'-bis(2-ethanesulfonic acid)), MOPSO (3-(N-morpholino)-2-hydroxypropanesulfonic acid), BIS-TRIS PROPANE (1,3-bis(tris(hydroxy-methyl)methylamino)propane), BES (N,N-bis(2-hydroxyethyl)-2-amino-ethanesulfonaic acid), MOPS (3-(N-morpholino)propanesulfonic acid), TES (N-tris(hydroxymethyl)methyl-2-aminoethanesulfonic acid), HEPES (N-(2-hydroxyethyl)piperazine-N'-(2-eth-anesulfonic acid), DIPSO (3-(N,N-bis(2-hydroxyethyl)amino)-2-hydroxypropan-esulfonicacid), MOBS (4-(N-morpholino)butanesulfonic acid), TAPSO (3-(N-tris(hydroxymethyl)methyl-amino)-2-hydroxypropanesulfonic acid), TRIZMA® (tris(hydroxymethyl-aminomethane), HEPPSO(N-(2-hydroxyethyl)piperazine-N'-(2-hydroxypropanesulfonic acid), POPSO (piperazine-N,N'-bis(2-hydroxypropane-sulfonic acid)), TEA (triethanolamine), EPPS (N-(2-hydroxyethyl)-piperazine-N'-(3-propanesulfonic acid), TRICINE (N-tris(hydroxy-methyl)methylglycine), GLY-GLY (glycylglycine), BICINE (N,N-bis(2-hydroxyethyl)glycine), HEPBS (N-(2-hydroxyethyl)piperazine-N'-(4-butanesulfonic acid)), TAPS(N-tris(hydroxymethyl)methyl-3-amino-propanesulfonic acid), AMPD (2-amino-2-methyl-1,3-propanediol), and/or any other buffers known to those of skill in the art. In one embodiment, the buffer is citric acid/phosphate buffer, acetate buffer, citrate buffer or phosphate buffer. In another embodiment, the buffer is a citrate buffer (citric acid/sodium citrate). The buffer concentration has been found herein to affect the stability of the composition. Buffer concentrations for use herein include from about 0 or 0.01 mM to about 150 mM, or about 1 mM to about 20 mM. In one embodiment, the buffer concentration is about 5 mM. In another embodiment, the buffer concentration is about 1 mM to about 50 mM, or about 20 mM. The kinetic-pH profile of formoterol is dependent on buffer concentration. At low and approximately neutral conditions, increasing the buffer concentration from 5 mM to 20 mM increased the rate constant of decomposition significantly. However, no noticeable differences in rate constant were observed in the pH region of about 4.5 to about 5.5 with increasing buffer concentration from 5 mM to 20 mM. The particular buffer and buffer concentration of a given composition for long term storage provided herein may be determined empirically using standard stability assays well known to those of skill in the art (see, e.g., the Examples).

The ionic strength of the compositions provided herein also has been found herein to affect the stability of the composition. Ionic strengths of the compositions provided herein are from about 0 to about 0.4, or from about 0.05 to about 0.16. Compositions having a lower ionic strength exhibit improved stability over formulations having higher ionic strength. The rate constant of decomposition was essentially the same at ionic strength 0.05 to 0.1, but increased to some extent at ionic strength of 0.2. The particular ionic strength of a given composition for long term storage provided herein may be determined empirically using standard stability assays well known to those of skill in the art (see, e.g., the Examples).

In embodiments where the pharamacologically suitable fluid is a saline solution, tonicity adjusting agents may be added to provide the desired ionic strength. Tonicity adjusting agents for use herein include those which display no or only negligible pharmacological activity after administration. Both inorganic and organic tonicity adjusting agents may be used in the compositions provided herein. Tonicity adjusting agents include, but are not limited to, ammonium carbonate, ammonium chloride, ammonium lactate, ammonium nitrate, ammonium phosphate, ammonium sulfate, ascorbic acid, bismuth sodium tartrate, boric acid, calcium chloride, calcium disodium edetate, calcium gluconate, calcium lactate, citric acid, dextrose, diethanolamine, dimethylsulfoxide, edetate disodium, edetate trisodium monohydrate, fluorescein sodium, fructose, galactose, glycerin, lactic acid, lactose, magnesium chloride, magnesium sulfate, mannitol, polyethylene glycol, potassium acetate, potassium chlorate, potassium chloride, potassium iodide, potassium nitrate, potassium phosphate, potassium sulfate, propylene glycol, silver nitrate, sodium acetate, sodium bicarbonate, sodium biphosphate, sodium bisulfite, sodium borate, sodium bromide, sodium cacodylate, sodium carbonate, sodium chloride, sodium citrate, sodium iodide, sodium lactate, sodium metabisulfite, sodium nitrate, sodium nitrite, sodium phosphate, sodium propionate, sodium succinate, sodium sulfate, sodium sulfite, sodium tartrate, sodium thiosulfate, sorbitol, sucrose, tartaric acid, triethanolamine, urea, urethan, uridine and zinc sulfate. In certain embodiments, the tonicity adjusting agent is sodium chloride, which is present at a concentration of from about 0 mg/mL to about 10, 15 or 20 mg/mL. In further embodiments, the compositions contain sodium chloride at a concentration of from about 0 mg/mL to about 7.5 mg/mL. In another embodiment, the compositions contain sodium chloride at a concentration of 0 mg/mL, 1.5 mg/mL, 6.8 mg/mL or 7.5 mg/mL. In these embodiments, the pharmacologically suitable fluid is aqueous saline.

The storage temperature of the compositions provided herein also has been found herein to affect the stability of the composition. Compositions stored at a lower temperature exhibit improved stability over formulations stored at higher temperatures. The effect of temperature on the rate constant of decomposition at pH 5, a buffer concentration of 5 mM, and an ionic strength of 0.05, was linear according to Arrhenius kinetics, i.e., when Ln $k_{obs}$ was plotted against 1/T, where T is the temperature in degree Kelvin.

The estimated shelf-life of formoterol in the compositions provided herein is significantly greater than that reported for known formoterol compositions. The estimated shelf-life of formoterol in the compositions provided herein is about 6.2 years at 5° C. and about 7.5 months at 25° C. The estimated formoterol concentrations in the compositions provided herein as a function of storage time at 5° C. and usage time at 25° C. was determined. It is estimated that greater than 90% of the initial formoterol present in the composition remains after 3 months of usage time at 25° C. and 3 years of storage time at 5° C. as well as after 0.5 months of usage time at 25° C. and 1 year of storage time at 5° C.

In certain embodiments, the compositions provided herein are prepared containing formoterol fumarate at a nominal concentration of 0.1 mg/mL at the indicated pH and citric acid/phosphate buffer concentrations. The solutions were stored at 60° C. In these compositions, formoterol is relatively more stable at a pH from about 4 to about 5, and is also more stable at lower buffer concentration.

The compositions provided herein also may include excipients and additives. The particular excipient or additive for use in the compositions for long term storage provided herein may be determined empirically using methods well known to those of skill in the art (see, e.g., the Examples). Excipients and additives are any pharmacologically suitable and therapeutically useful substance which is not an active substance. Excipients and additives generally have no pharmacological activity, or at least no undesirable pharmacological activity. The excipients and additives include, but are not limited to, surfactants, stabilizers, complexing agents, antioxidants, or preservatives which prolong the duration of use of the finished pharmaceutical formulation, flavorings, vitamins, or other additives known in the art. Complexing agents include, but are not limited to, ethylenediaminetetraacetic acid (EDTA) or a salt thereof, such as the disodium salt, citric acid, nitrilotriacetic acid and the salts thereof. In one embodiment, the complexing agent is EDTA. In another embodiment, particularly in the suspension formulations provided herein, the complexing agent is sodium edetate. In these embodiments, the compositions contain sodium edetate at a concentration of about 0.05 mg/mL to about 0.5 mg/mL, or about 0.1 mg/mL to about 0.2 mg/mL.

Preservatives include, but are not limited to, those that protect the solution from contamination with pathogenic particles, including benzalkonium chloride or benzoic acid, or benzoates such as sodium benzoate. Antioxidants include, but are not limited to, vitamins, provitamins, ascorbic acid, vitamin E or salts or esters thereof.

In certain embodiments herein, particularly in the solution formulations provided herein, the compositions contain vitamin E TPGS (d-α-tocopheryl polyethylene glycol 1000 succinate). In these embodiments, vitamin E TPGS is present at a concentration of about 0 mg/mL to about 100 mg/mL, or about 5 mg/mL to about 50 mg/mL. In certain embodiments herein, the compositions contain vitamin E TPGS at a concentration of 10 mg/mL, 20 mg/mL, 30 mg/mL or 50 mg/mL.

The compositions provided herein also may include a cosolvent, which increases the solubility of additives or the active ingredient(s). The particular cosolvent for use in the compositions for long term storage provided herein may be determined empirically using methods well known to those of skill in the art (see, e.g., the Examples). Cosolvents for use herein include, but are not limited to, hydroxylated solvents or other polar solvents, such as alcohols such as isopropyl alcohol, glycols such as propylene glycol, polyethylene glycol, polypropylene glycol, glycol ether, glycerol, and polyoxyethylene alcohols. In certain embodiments herein, particularly in the solution formulations provided herein, the compositions contain a glycol. In other embodiments, the compositions contain propylene glycol and/or polyethylene glycol, including polyethylene glycol 400. In these embodiments, the glycol is present at a concentration of about 0 mg/mL to about 100 mg/mL, or about 5 mg/mL to about 50 mg/mL. In further embodiments, the compositions contain propylene glycol at a concentration of 17 mg/mL or 20 mg/mL. In other embodiments, the compositions contain polyethylene glycol 400 at a concentration of 10 mg/mL, 20 mg/mL, 30 mg/mL or 50 mg/mL.

The compositions provided herein, particularly the suspension formulations provided herein, may also contain one or more emulsifiers. The particular emulsifier for use in the compositions for long term storage provided herein may be determined empirically using methods well known to those of skill in the art (see, e.g., the Examples). Emulsifiers for use herein include, but are not limited to, polyoxyetheylene sorbitan fatty esters or polysorbates, including, but not limited to, polyethylene sorbitan monooleate (Polysorbate 80), polysorbate 20 (polyoxyethylene (20) sorbitan monolaurate), polysorbate 65 (polyoxyethylene (20) sorbitan tristearate), polyoxyethylene (20) sorbitan mono-oleate, polyoxyethylene (20) sorbitan monopalmitate, polyoxyethylene (20) sorbitan monostearate; lecithins; alginic acid; sodium alginate; potassium alginate; ammonium alginate; calcium alginate; propane-1,2-diol alginate; agar; carrageenan; locust bean gum; guar gum; tragacanth; acacia; xanthan gum; karaya gum; pectin; amidated pectin; ammonium phosphatides; microcrystalline cellulose; methylcellulose; hydroxypropylcellulose; hydroxypropylmethylcellulose; ethylmethylcellulose; carboxymethylcellulose; sodium, potassium and calcium salts of fatty acids; mono- and di-glycerides of fatty acids; acetic acid esters of mono- and di-glycerides of fatty acids; lactic acid esters of mono- and di-glycerides of fatty acids; citric acid esters of mono- and di-glycerides of fatty acids; tartaric acid esters of mono- and di-glycerides of fatty acids; mono- and diacetyltartaric acid esters of mono- and di-glycerides of fatty acids; mixed acetic and tartaric acid esters of mono- and di-glycerides of fatty acids; sucrose esters of fatty acids; sucroglycerides; polyglycerol esters of fatty acids; polyglycerol esters of polycondensed fatty acids of castor oil; propane-1,2-diol esters of fatty acids; sodium stearoyl-2-lactylate; calcium stearoyl-2-lactylate; stearoyl tartrate; sorbitan monostearate; sorbitan tristearate; sorbitan monolaurate; sorbitan mono-oleate; sorbitan monopalmitate; extract of quillaia; polyglycerol esters of dimerised fatty acids of soya bean oil; oxidatively polymerised soya bean oil; and pectin extract.

In certain embodiments herein, the emulsifier(s) is (are) a polyoxyetheylene sorbitan fatty ester or polysorbate, including, but not limited to, polyethylene sorbitan monooleate (Polysorbate 80), polysorbate 20 (polyoxyethylene (20) sorbitan monolaurate), polysorbate 65 (polyoxyethylene (20) sorbitan tristearate), polyoxyethylene (20) sorbitan monooleate, polyoxyethylene (20) sorbitan monopalmitate, polyoxyethylene (20) sorbitan monostearate; sorbitan monostearate; sorbitan tristearate; sorbitan monolaurate; sorbitan mono-oleate; or jsorbitan monopalmitate. In further embodiments, the emulsifier(s) is (are) polysorbate 80, sorbitan monolaruate or polyoxyethylene (20) sorbitan monolaurate.

C. Preparation of Compounds for Use in the Compositions

The preparation of the compounds used in the compositions provided herein is described below. Any such compound or similar compound may be synthesized according to a method discussed in general below or by only minor modification of the methods by selecting appropriate starting materials.

Formoterol may be prepared according to the method disclosed in U.S. Pat. No. 3,994,974. Briefly, 4-benzyloxy-3-nitro-α-bromoacetophenone is reacted with N-benzyl-N-(1-methyl-2-p-methoxyphenylethyl)amine to form the α-aminoacetophenone. This compound was subjected to the following series of reactions: (i) reduction of the ketone with sodium borohydride; (ii) reduction of the nitro group with aqueous hydrochloric acid and iron powder; (iii) amine formylation with acetic anhydride and formic acid; and (iv) catalytic reduction over 10% palladium on carbon to afford formoterol free base. Crystallization of the ½ fumarate salt from ethanol provides (formoterol)*½ fumarate.

The individual enantiomers of formoterol, 2-hydroxy-5-((1S)-1-hydroxy-2-(((1S)-2-(p-methoxyphenyl)-1-methylethyl)amino)ethyl)formanilide and 2-hydroxy-5-((1R)-1-hydroxy-2-(((1R)-2-(p-methoxyphenyl)-1-methylethyl)amino)ethyl)formanilide, may be prepared by the method disclosed in U.S. Pat. No. 6,040,344. Briefly, reaction of optically pure 4-benzyloxy-3-formamidostyrene oxide with an optically pure 4-methoxy-α-methyl-N-(phenylmethyl)benzeneethanamine, followed by debenzylation, affords the desired enantiomer of formoterol. Debenzylation may be accomplished by reduction with hydrogen gas in the presence of a noble metal catalyst, such as palladium on carbon.

The required optically pure 4-benzyloxy-3-formamidostyrene oxide may be prepared from 4-benzyloxy-3-nitro-α-bromoacetophenone by (i) reduction with vorane in the presence of an optically pure aminoindanol, (ii) hydrogenation over platinum oxide catalyst, (iii) formylation with formic acid and acetic anhydride, and (iv) epoxide formation in the presence of potassium carbonate.

The required optically pure 4-methoxy-α-methyl-N-(phenylmethyl)-benzeneethanamine may be prepared from 4-methoxyphenylacetone by (i) reductive amination with benzylamine in the presence of hydrogen and a platinum catalyst, and (ii) crystallization of the desired optically pure amine from the resulting racemic mixture as its mandelic acid salt.

Budesonide may be synthesized by the procedure disclosed in U.S. Pat. No. 3,929,768. Briefly, reaction of triamcinolon with propionaldehyde and catalyic perchloric acid in dry dioxane at ambient temperature provides, following chromatography on hydroxy-propylated, cross-linked dextran gel, budesonide.

Fluticasone propionate may be synthesized by the procedure disclosed in U.S. Pat. No. 4,335,121. Briefly, the corresponding carbothioic acid is prepared from the carboxylic acid precursor by reaction with dimethylthiocarbamoyl chloride in the presence of triethylamine. Reaction with bromochloromethane and sodium hydrogen carbonate in dimethylacetamide affords the corresponding S-chloromethyl carbothioate. This compound is treated with sodium iodide in acetone to give the corresponding S-iodomethyl carbothioate. Fluoride substitution of the iodo group is accomplished by reaction with silver fluoride in acetonitrile to afford the desired compound.

D. Formulation of Pharmaceutical Compositions

The compositions provided herein are prepared by procedures well known to those of skill in the art. For example, a solution formulations may be prepared by the procedure of EXAMPLE 1. Briefly, polyethylene glycol 400 and/or propylene glycol, and a preservative, such as vitamin E TPGS, are mixed at about 42° C. until a homogeneous solution forms. The temperature is lowered and the steroidal anti-inflammatory agent is added. In a second vessel, formoterol fumarate dihydrate and the remaining ingredients are dissolved in approximately 70% water. The two solutions are mixed and the resulting solution is diluted with water to the desired volume.

Suspension formulations are prepared by the procedure of EXAMPLE 2. Briefly, all ingredients other than the steroidal anti-inflammatory agent and formoterol fumarate dihydrate are dissolved in about 40% water with mixing. The steroidal anti-inflammatory agent, which is micronized, is dispersed in the above mixture with high speed homogenization. Formoterol fumarate dihydrate is dissolved in 50% water and added to the steroidal suspension with mixing until a uniform suspension forms.

E. Evaluation of the Activity of the Compositions

Standard physiological, pharmacological and biochemical procedures are available for testing the compositions provided herein to identify those that possess bronchodilatory activity.

In vitro and in vivo assays that may be used to evaluate bronchodilatory activity are well known to those of skill in the art. See also, e.g., U.S. Pat. Nos. 3,994,974, and 6,068,833; German Patent No. 2,305,092; Kaumann et al. (1985) *Naunyn-Schmied Arch. Pharmacol.* 331:27-39; Lemoine et al. (1985) *Naunyn-Schmied Arch. Pharmacol.* 331:40-51; Tomioka et al. (1981) *Arch. Int. Pharmacodyn.* 250:279-292; Dellamary et al. (2000) *Pharm. Res.* 17(21:168-174; Rico-Mendez et al. (1999) *Rev. Alerg. Mex.* 46(51:130-135; Seberova et al. (2000) *Respir. Med.* 94(6):607-611; Lotvall et al. (1999) *Can. Respir. J.* 6(5):412-416; Campbell et al. (1999) *Respir. Med.* 93(41:236-244; Nightingale et al., (1999) *Am. J. Respir. Crit. Care Med.* 159(6):1786-1790; Lecaillon et al. (1999) *Eur. J. Clin. Pharmacol.* 55(2):131-138; Bartow et al. (1998) *Drugs* 55(2):303-322; Ekstrom et al. (1998) *Respir. Med.* 92(8):1040-1045; Ringdal et al. (1998) *Respir. Med.* 92(81:1017-1021; Totterman et al. (1998) *Eur. Respir. J.* 12(31:573-579; Palmqvist et al. (1997) *Eur. Respir. J.* 10(1/1:2484-2489; Nielsen et al. (1997) *Eur. Respir. J.* 10(9):2105-2109; Ullman et al. (1996) *Allergy* 51(101:745-748; Selroos et al. (1996) *Clin. Immunother.* 6:273-299; and Schreurs et al., (1996) *Eur. Respir. J.* 9(81: 1678-1683.

F. Methods of Treatment of Bronchoconstrictive Disorders

The compositions provided herein are used for treating, preventing, or ameliorating one or more symptoms of a bronchoconstrictive disorders in a subject. In one embodiment, the method includes administering to a subject an effective amount of a composition containing $\beta_2$-adrenoreceptor agonist, including, but not limited to, formoterol, and a steroidal anti-inflammatory agent, including, but not limited to, budesonide and fluticasone propionate, whereby the disease or disorder is treated or prevented, or one or more symptoms are ameliorated. The subject treated is, in certain embodiments, a mammal. In certain of these embodiments, the mammal is a human.

In another embodiment, the method provided herein includes oral administration of a composition provided herein. In certain embodiments herein, the composition is directly administered to a subject in need of such treatment via nebulization without dilution or other modification of the composition prior to administration.

The methods for treatment, prevention, or amelioration of one or more symptoms of bronchoconstrictive disorders, in another embodiment, further include administering one or more of (a), (b) or (c) as follows: (a) a $\beta_2$-adrenoreceptor agonist; (b) a dopamine ($D_2$) receptor agonist; or (c) an anticholinergic agent; simultaneously with, prior to or subsequent to the composition provided herein.

$\beta_2$-Adrenoreceptor agonists for use in combination with the compositions provided herein include, but are not limited to, Albuterol ($\alpha^1$-(((1,1-dimethylethyl)amino)methyl)-4-hydroxy-1,3-benzenedimethanol); Bambuterol (dimethylcarbamic acid 5-(2-((1,1-dimethylethyl)amino)-1-hydroxyethyl)-1,3-phenylene ester); Bitolterol (4-methylbenzoic acid 4-(2-((1,1-dimethylethyl)amino)-1-hydroxyethyl)-1,2-phenylene ester); Broxaterol (3-bromo-α-(((1,1-dimethylethyl) amino)methyl)-5-isoxazolemethanol); Isoproterenol (4-(1-hydroxy-2-((1-methylethyl)amino)ethyl)-1,2-benzenediol); Trimetoquinol (1,2,3,4-tetrahydro-1-((3,4,5-trimethoxyphenyl)methyl)-6,7-isoquinolinediol); Clenbuterol (4-amino-3,5-dichloro-α-(((1,1-dimethylethyl)amino)methyl)benzenemethanol); Fenoterol (5-(1-hydroxy-2-((2-(4-hydroxyphenyl)-1-methylethyl)amino)ethyl)-1,3-benzenediol); Formoterol (2-hydroxy-5-((1RS)-1-hydroxy-2-1((1RS)-2-(p-methoxyphenyl)-1-methylethyl)amino) ethyl)formanilide); (R,R)-Formoterol; Desformoterol ((R,R) or (S,S)-3-amino-4-hydroxy-α-(((2-(4-methoxyphenyl)-1-methylethyl)amino)methyl)benzenemethanol); Hexoprenaline (4,4'-(1,6-hexanediyl)-bis(imino(1-hydroxy-2,1-ethanediyl)))bis-1,2-benzenediol); Isoetharine (4-(1-hydroxy-2-((1-methylethyl)amino)butyl)-1,2-benzenediol); Isoprenaline (4-(1-hydroxy-2-((1-methylethyl)amino) ethyl)-1,2-benzenediol); Metaproterenol (5-(1-hydroxy-2-((1-methylethyl)amino)ethyl)-1,3-benzenediol); Picumeterol (4-amino-3,5-dichloro-α-(((6-(2-(2-pyridinyl)ethoxy) hexyl)amino)methyl)benzenemethanol); Pirbuterol ($\alpha^6$-(((1, 1-dimethylethyl)amino)methyl)-3-hydroxy-2,6-pyridinemethanol); Procaterol (((R*,S*)-(±)-8-hydroxy-5-(1-hydroxy-2-((1-methylethyl)amino)butyl)-2(1H)-quinolinone); Reproterol ((7-(3-((2-(3,5-dihydroxyphenyl)-2-hydroxyethyl)amino)propyl)-3,7-dihydro-1,3-dimethyl-1H-purine-2,6-dione); Rimiterol (4-(hydroxy-2-piperidinylmethyl)-1,2-benzenediol); Salbutamol ((±)-$\alpha^1$-(((1,1-dimethylethyl)amino)methyl)-4-hydroxy-1,3-benzenedimethanol); (R)-Salbutamol; Salmeterol ((±)-4-hydroxy-$\alpha^1$-(((6-(4-phenylbutoxy)hexyl)amino)methyl)-1, 3-benzenedimethanol); (R)-Salmeterol; Terbutaline (5-(2-((1,1-dimethylethyl)amino)-1-hydroxyethyl)-1,3-benzenediol); Tulobuterol (2-chloro-α-(((1,1-dimethylethyl) amino)methyl)benzenemethanol); and TA-2005 (8-hydroxy-5-((1R)-1-hydroxy-2-(N-((1R)-2-(4-methoxyphenyl)-1-methylethyl)amino)ethyl)carbostyril hydrochloride).

Dopamine ($D_2$) receptor agonists include, but are not limited to, Apomorphine ((r)-5,6,6a,7-tetrahydro-6-methyl-4H-dibenzo[de,g]quinoline-10,11-diol); Bromocriptine ((5'α)-2-bromo-12'-hydroxy-2'-(1-methylethyl)-5'-(2-methylpropyl) ergotaman-3',6',18-trione); Cabergoline ((8β)-N-(3-(dimethylamino)propyl)-N-((ethylamino)carbonyl)-6-(2-propenyl)ergoline-8-carboxamide); Lisuride (N'-((8α)-9,10-didehydro-6-methylergolin-8-yl)-N,N-diethylurea); Pergolide ((8β)-8-((methylthio)methyl)-6-propylergoline); Levodopa (3-hydroxy-L-tryrosine); Pramipexole ((s)-4,5,6, 7-tetrahydro-N$^6$-propyl-2,6-benzothiazolediamine); Quinpirole hydrochloride (trans-(-)-4aR-4,4a,5,6,7,8,8a,9-octahydro-5-propyl-1H-pyrazolo[3,4-g]quinoline hydrochloride); Ropinirole (4-(2-(dipropylamino)ethyl)-1,3-dihydro-2H-indol-2-one); and Talipexole (5,6,7,8-tetrahydro-6-(2-propenyl)-4H-thiazolo[4,5-d]azepin-2-amine). Other dopamine $D_2$ receptor agonists for use herein are disclosed in International Patent Application Publication No. WO 99/36095.

Anticholinergic agents for use herein include, but are not limited to, ipratropium bromide, oxitropium bromide, atropine methyl nitrate, atropine sulfate, ipratropium, belladonna extract, scopolamine, scopolamine methobromide, homatropine methobromide, hyoscyamine, isopriopramide, orphenadrine, benzalkonium chloride, tiotropium bromide and glycopyrronium bromide. In certain embodiments, the compositions contain an anticholinergic agent, such as ipratropium bromide or tiotropium bromide, at a concentration of about 5 µg/mL to about 5 mg/mL, or about 50 µg/mL to about 200 µg/mL. In other embodiments, the compositions for use in the methods herein contain an anticholinergic agent, including ipratropium bromide and tiotropium bromide, at a concentration of about 83 µg/mL or about 167 µg/mL.

Other active ingredients for use herein in combination therapy, include, but are not limited to, IL-5 inhibitors such as those disclosed in U.S. Pat. Nos. 5,668,110, 5,683,983, 5,677, 280 and 5,654,276; antisense modulators of IL-5 such as those disclosed in U.S. Pat. No. 6,136,603; milrinone (1,6-dihydro-2-methyl-6-oxo-(3,4'-bipyridine)-5-carbonitrile); milrinone lactate; tryptase inhibitors such as those disclosed in U.S. Pat. No. 5,525,623; tachykinin receptor antagonists such as those disclosed in U.S. Pat. Nos. 5,691,336, 5,877, 191, 5,929,094, 5,750,549 and 5,780,467; leukotriene receptor antagonists such as montelukast sodium (Singular®, R-(E)]-1-[[[1-[3-[2-(7-chloro-2-quinolinyl)ethenyl]phenyl]-3-[2-(1-hydroxy-1-methylethyl)phenyl]-propyl]thio]methyl]cyclopropaneacetic acid, monosodium salt), 5-lypoxygenase inhibitors such as zileuton (Zyflo®, Abbott Laboratories, Abbott Park, Ill.), and anti-IgE antibodies such as Xolair® (recombinant humanized anti-IgE monoclonal antibody (CGP 51901; IGE 025A; rhuMAb-E25), Genentech, Inc.).

The bronchoconstrictive disorder to be treated, prevented, or whose one or more symptoms are to be ameliorated is associated with asthma, including, but not limited to, bronchial asthma, allergic asthma and intrinsic asthma, e.g., late asthma and airway hyper-responsiveness; and, particularly in embodiments where an anticholinergic agent is used, other chronic obstructive pulmonary diseases (COPDs), including, but not limited to, chronic bronchitis, emphysema, and associated cor pulmonale (heart disease secondary to disease of the lungs and respiratory system) with pulmonary hypertension, right ventricular hypertrophy and right heart failure. COPD is frequently associated with cigarette smoking, infections, environmental pollution and occupational dust exposure.

G. Nebulizers

The compositions provided herein are intended for administration to a subject in need of such treatment via nebulization. Nebulizers that nebulize liquid formulations containing no propellant are suitable for use with the compositions provided herein. Nebulizers are available from, e.g., Pari GmbH (Starnberg, Germany), DeVilbiss Healthcare (Heston, Middlesex, UK), Healthdyne, Vital Signs, Baxter, Allied Health Care, Invacare, Hudson, Siemens, Aerogen, Omron, Bremed, AirSep, Luminscope, Medisana, Mountain Medical, Aerosol Medical Ltd. (Colchester, Essex, UK), AFP Medical (Rugby, Warwickshire, UK), Bard Ltd. (Sunderland, UK), Carri-Med. Ltd. (Dorking, UK), Plaem Nuiva (Brescia, Italy), Henleys Medical Supplies (London, UK), Intersurgical (Berkshire, UK), Lifecare Hospital Supplies (Leies, UK), Medic-Aid Ltd. (West Sussex, UK), Medix Ltd. (Essex, UK), Sinclair Medical Ltd. (Surrey, UK), and many others.

Nebulizers for use herein include, but are not limited to, jet nebulizers (optionally sold with compressors), ultrasonic nebulizers, and others. Exemplary jet nebulizers for use herein include Pari LC plus/ProNeb, Pari LC plus/ProNeb Turbo, Pari LC plus/Dura Neb 1000 & 2000, Pari LC plus/Walkhaler, Pari LC plus/Pari Master, Pari LC star, Omron CompAir XL Portable Nebulizer System (NE-C18 and JETAir Disposable nebulizer), Omron CompAir Elite Compressor Nebulizer System (NE-C21 and Elite Air Reusable Nebulizer), Pari LC Plus or Pari LC Star nebulizer with Proneb Ultra compressor, Pulmo-aide, Pulmo-aide LT, Pulmo-aide traveler, Invacare Passport, Inspiration Healthdyne 626, Pulmo-Neb Traverler, DeVilbiss 646, Whisper Jet, Acorn II, Misty-Neb, Allied aerosol, Schuco Home Care, Lexan Plasic Pocet Neb, SideStream Hand Held Neb, Mobil Mist, Up-Draft, Up-Draft II, T Up-Draft, ISO-NEB, AVA-NEB, Micro Mist, and PulmoMate. Exemplary ultrasonic nebulizers for use herein include MicroAir, UltraAir, CompAir, Pulmosonic, Scout, 5003 Ultrasonic Neb, 5110 Ultrasonic Neb, 5004 Desk Ultrasonic Nebulizer, Mystique Ultrasonic, Siemens Ultra Nebulizer 145, Luminscope's Ultrasonic Nebulizer, Medisana Ultrasonic Nebulizer, Microstat Ultrasonic Nebulizer, and MABISMist Hand Held Ultrasonic Nebulizer. Other nebulizers for use herein include 5000 Electromagnetic Neb, Aeroneb™ Partable Nebulizer System, Aerodose™ Inhaler, 5001 Electromagnetic Neb 5002, Rotary Piston Neb, Lumineb I Piston Nebulizer 5500, and AeroEclipse Breath Actuated Nebulizer.

H. Articles of Manufacture

The compositions provided herein may be packaged as articles of manufacture containing packaging material, a composition provided herein, which is useful for treatment, prevention or amelioration of one or more symptoms of diseases or disorders associated with undesired and/or uncontrolled bronchoconstriction, and a label that indicates that the composition is used for treatment, prevention or amelioration of one or more symptoms of diseases or disorders associated with undesired and/or uncontrolled bronchoconstriction.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment.

In one embodiment herein, the compositions are packaged with a nebulizer for direct administration of the composition to a subject in need thereof.

The following examples are included for illustrative purposes only and are not intended to limit the scope of the invention.

Example 1

Preparation of Solution Formulations

Polyethylene glycol 400 and/or propylene glycol and vitamin E TPGS were mixed in a stainless steel container with heating at about 42° C. until a homogeneous liquid formed. While maintaining the liquid phase, the temperature was lowered and the steroid active ingredient, e.g., budesonide or fluticasone propionate, was added. The mixing was continued until all of the drug substance had dissolved. In another container all other ingredients, including formoterol fumarate dihydrate, were mixed with about 70% water until a clear solution formed. The two solutions were mixed together until a homogeneous clear solution formed. The volume was made up with water and the solution was mixed to give the desired composition.

Using the above procedure, the following solution compositions containing the indicated ingredients in the indicated amounts were prepared. For each steroidal anti-inflammatory agent, a low strength and a high strength formulation was prepared.

Budesonide/Formoterol solution formulations

| Ingredient | Concentration | |
|---|---|---|
| | Low strength | High strength |
| Formoterol fumarate dihydrate | 85 μg/mL | 170 μg/mL |
| Budesonide | 125 μg/mL | 250 μg/mL |
| Vitamin E TPGS | 10 mg/mL | 20 mg/mL |
| Either: | | |
| Propylene glycol or | 17 mg/mL | 20 mg/mL |
| Polyethylene glycol 400 | 10 mg/mL | 20 mg/mL |
| Citrate buffer | 5 mM | 5 mM |
| Sodium Chloride | 7.5 mg/mL | 6.8 mg/mL |
| Water | q.s. | q.s. |

Fluticasone propionate/Formoterol solution formulations

| Ingredient | Concentration | |
|---|---|---|
| | Low strength | High strength |
| Formoterol fumarate dihydrate | 85 μg/mL | 170 μg/mL |
| Fluticasone propionate | 125 μg/mL | 250 μg/mL |
| Vitamin E TPGS | 30 mg/mL | 50 mg/mL |
| Either: | | |
| Propylene glycol or | 17 mg/mL | 20 mg/mL |
| Polyethylene glycol 400 | 30 mg/mL | 50 mg/mL |
| Citrate buffer | 5 mM | 5 mM |
| Sodium Chloride | 1.5 mg/mL | 0 mg/mL |
| Water | q.s. | q.s. |

Example 2

Preparation of Suspension Formulations

All ingredients, with the exception of formoterol fumarate dihydrate and the steroidal anti-inflammatory agent, e.g., budesonide or fluticasone propionate, were dissolved in about 40% water in a container with mixing. The steroidal active ingredient was added and the mixture was dispersed with high speed homogenization. Formoterol fumarate dihydrate was dissolved in about 50% water with mixing and the resulting solution was added to the steroidal suspension with mixing until a uniform suspension formed.

Using the above procedure, the following suspension formulations containing the indicated ingredients in the indicated amounts were prepared.

Budesonide/Formoterol suspension formulations

| Ingredient | Concentration |
|---|---|
| Formoterol fumarate dihydrate | 5-2000 µg/mL or 50-200 µg/mL |
| Budesonide | 125-500 µg/mL |
| Disodium edetate | 0.1-0.2 mg/mL |
| Polysorbate 80 | 0.2-0.3 mg/mL |
| Sodium chloride | 5-10 mg/mL |
| Citrate buffer | 1-20 mM |
| Water | q.s. |

Fluticasone propionate/Formoterol suspension formulations

| Ingredient | Concentration |
|---|---|
| Formoterol fumarate dihydrate | 5-2000 µg/mL or 50-200 µg/mL |
| Fluticasone propionate micronized | 250-1000 µg/mL |
| Sorbitan monolaurate | 0.05-0.2 mg/mL |
| Polyoxyethylene 20 sorbitan monolaurate | 0.1-0.3 mg/mL |
| Sodium chloride | 5-10 mg/mL |
| Citrate buffer | 1-20 mM |
| Water | q.s. |

Since modifications will be apparent to those of skill in this art, it is intended that this invention be limited only by the scope of the appended claims.

We claim:

1. A method for treating or ameliorting one or more symptoms of a bronchoconstrictive disorder comprising: providing a pharmaceutical composition packaged for single dosage administration, the composition including (i) formoterol, or a pharmaceutically acceptable salt or hydrate thereof in solution; and (ii) a steroidal anti-inflammatory agent, or a pharmaceutically acceptable salt thereof in suspension; in a pharmacologically suitable fluid comprising water that is propellant-free; the composition as formulated has an estimated shelf-life of greater than 1 month usage time at 25° C. and greater than or equal to 1 year storage time when stored at 5° C., whereby greater than 90% of the initial amount of formoterol in the compositions remains at such time; and the formoterol free base concentration is about 5 µg/mL to about 200 µg/mL, whereby the composition is formulated for direct administration to a subject in need thereof; and without dilution, directly administering an effective amount of the composition as provided to a subject in need of such treatment.

2. The method of claim 1, wherein greater than about 80% of the initial formoterol is present in the composition after 1 month usage time at 25° C. and 1 year storage time at 5° C.

3. The method of claim 1, wherein the pharmacologically suitable fluid further comprises a polar solvent.

4. The method of claim 3, wherein the polar solvent is a protic solvent.

5. The method of claim 4, wherein the composition further comprises a tonicity adjusting agent.

6. The method of claim 5, wherein the tonicity adjusting agent is ammonium carbonate, ammonium chloride, ammonium lactate, ammonium nitrate, ammonium phosphate, ammonium sulfate, ascorbic acid, bismuth sodium tartrate, boric acid, calcium chloride, calcium disodium edetate, calcium gluconate, calcium lactate, citric acid, dextrose, diethanolamine, dimethylsulfoxide, edetate disodium, edetate trisodium monohydrate, fluorescein sodium, fructose, galactose, glycerin, lactic acid, lactose, magnesium chloride, magnesium sulfate, mannitol, polyethylene glycol, potassium acetate, potassium chlorate, potassium chloride, potassium iodide, potassium nitrate, potassium phosphate, potassium sulfate, proplyene glycol, silver nitrate, sodium acetate, sodium bicarbonate, sodium biphosphate, sodium bisulfite, sodium borate, sodium bromide, sodium cacodylate, sodium carbonate, sodium chloride, sodium citrate, sodium iodide, sodium lactate, sodium metabisulfite, sodium nitrate, sodium nitrite, sodium phosphate, sodium propionate, sodium succinate, sodium sulfate, sodium sulfite, sodium tartrate, sodium thiosulfate, sorbitol, sucrose, tartaric acid, triethanolamine, urea, urethan, uridine or zinc sulfate.

7. The method of claim 6, wherein the tonicity adjusting agent is sodium chloride.

8. The method of claim 1, wherein the pharmacologically suitable fluid comprises a buffer.

9. The method of claim 8, wherein the buffer is citric acid/phosphate, acetate, barbital, borate, cacodylate, citrate, collidine, formate, maleate, phosphate, succinate, citrate-phosphate-borate (Teorell-Stanhagen), veronal acetate, MES (2-(N-morpholino)ethanesulfonic acid), BIS-TRIS (bis(2-hydroxyethyl)iminotris(hydroxylmethyl)methane), ADA (N-(2-acetamido)-2-iminodiacetic acid), ACES (N-(carbamoylmethyl)-2-aminoethanesulfonaic acid), PIPES (piperazine-N,N'-bis(2-ethanesulfonic acid)), MOPSO (3-(N-morpholino)-2-hydroxypropanesulfonic acid), BIS-TRIS PROPANE (1,3-bis(tris(hydroxymethyl)methylamino)propane), BES (N,N-bis(2-hydroxyethyl)-2-aminoethanesulfonaic acid), MOPS (3-(N-morpholino)propanesulfonic acid), TES (N-tris(hydroxylmethyl)methyl-2-aminoethanesulfonic acid), HEPES (N-(2-hydroxyethyl)piperazine-N'-(2-ethanesulfonic acid), DIPSO (3-(N,N-bis(2-hydroxyethyl)amino)-2-hydroxypropanesulfonic acid), MOBS (4-(N-morpholino)butanesulfonic acid), TAPSO (3-(N-tris(hydroxylmethyl)methylamino)-2-hydroxypropanesulfonic acid), tris(hydroxymethylaminomethane, HEPPSO(N-(2-hydroxyethyl)piperazine-N'-(2-hydroxypropanesulfonic acid), POPSO (piperazine-N,N'-bis(2-hydroxypropane-sulfonicacid)), TEA (triethanolamine), EPPS(N-(2-hydroxyethyl) piperazine-N'-(3-propanesulfonic acid), TRICINE (N-tris (hydroxylmethyl)methylglycine) GLY-GLY (glycyl glycine), BICINE (N,N-bis(2-hydroxyethyl)glycine), HEPBS (N-(2-hydroxyethyl)piperazine-N'-(4-butanesulfonic acid)), TAPS(N-tris(hydroxy-methyl)methyl-3-aminopropanesulfonic acid), or AMPD (2-amino-2-methyl-1,3-propanediol) buffer.

10. The method of claim 9, wherein the buffer is citrate buffer.

11. The method of claim 10, wherein the buffer concentration is from about 0.01 mM to about 150 mM.

12. The method of claim 11, wherein the buffer concentration is from what 1 mM to about 20 mM.

13. The method of claim 12, wherein the buffer concentration is about 5 mM.

14. The method of claim 6, wherein the ionic strength of the composition is about 0 to about 0.4.

15. The method of claim 14, wherein the ionic strength of the composition is about 0.05 to about 0.16.

16. The method of claim 1, wherein the pH of the composition is about 2.0 to about 8.0.

17. The method of claim 16, wherein the pH of the composition is about 4.0 to about 6.0.

18. The method of claim 17, wherein the pH of the composition is about 4.5 to about 5.5.

19. The method of claim 18, wherein the pH of the composition is about 5.0.

20. The method of claim 1, wherein the formoterol free base concentration in the composition is about 10 μg/mL to about 200 μg/mL.

21. The method of claim 20, wherein the formoterol free base concentration in the composition is about 50 μg/mL to about 200 μg/mL.

22. The method of claim 21, wherein the formoterol free base concentration in the composition is about 59 μg/mL.

23. The method of claim 21, wherein the formoterol free base concentration in the composition is about 118 μg/mL.

24. The method of claim 6, wherein the composition further comprises a buffer.

25. The method of claim 24, wherein the buffer is citric acid/phosphate, acetate, barbital, borate, cacodylate, citrate, collidine, formate, maleate, phosphate, succinate, citrate-phosphate-borate (Teorell-Stanhagen), veronal acetate, MES (2-(N-morpholino)ethanesulfonic acid), BIS-TRIS (bis(2-hydroxyethyl)iminotris-(hydroxylmethyl)methane), ADA (N-(2-acetamido)-2-iminodiacetic acid), ACES (N-(carbamoylmethyl)-2-aminoethanesulfonaic acid), PIPES (piperazine-N,N'-bis(2-ethanesulfonic acid)), MOPSO (3-(N-morpholino)-2-hydroxypropanesulfonic acid), BIS-TRIS PROPANE (1,3-bis(tris(hydroxymethyl)methylamino)propane), BES (N,N-bis(2-hydroxyethyl)-2-aminoethanesulfonaic acid), MOPS (3-(N-morpholino)propanesulfonic acid), TES (N-tris(hydroxymethyl)methyl-2-aminoethanesulfonic acid), HEPES (N-(2-hydroxyethyl)piperazine-N'-(2-ethanesulfonic acid), DIPSO (3-(N,N-bis(2-hydroxyethyl)amino)-2-hydroxypropanesulfonic acid), MOBS (4-(N-morpholino)-butanesulfonic acid), TAPSO (3-(N-tris(hydroxymethyl)methylamino)-2-hydroxypropanesulfonic acid), tris(hydroxymethylaminomethane, HEPPSO(N-(2-hydroxyethyl)piperazine-N'-(2-hydroxypropanesulfonicacid), POPSO (piperazine-N,N'-bis(2-hydroxypropane-sulfonic acid)), TEA (triethanolamine), EPPS(N-(2-hydroxyethyl) piperazine-N-(3-propanesulfonic acid), TRICINE (N-tris(hydroxylmethyl)methylglycine), GLY-GLY (glycylglycine), BICINE (N,N-bis(2-hydroxyethyl)glycine), HEPES (N-(2-hydroxyethyl)piperazine-N'-(4-butanesulfonic acid)), TAPS(N-tris(hydroxy-methyl)methyl-3-aminopropanesulfonic or AMPD (2 amino 2 methyl-3-propanediol)buffer.

26. The method of claim 25, wherein the buffer is citrate buffer.

27. The method of claim 26, wherein the buffer concentration is from about 0.01 mM to about 150 mM.

28. The method of claim 27, wherein the buffer concentration is from about 1 mM to about 20 mM.

29. The method of claim 28, wherein the buffer concentration is about 5 mM.

30. The method of claim 24, wherein the ionic strength of the composition is about 0 to about 0.4.

31. The method of claim 29, wherein the ionic strength of the composition is about 0.05 to about 0.16.

32. The method of claim 24, wherein the pH of the composition is about 2.0 to about 8.0.

33. The method of claim 32, wherein the pH of the composition is about 4.0 to about 6.0.

34. The method of claim 33, wherein the pH of the composition is about 4.5 to about 5.5.

35. The method of claim 34, wherein the pH of the composition is about 5.0.

36. The method of claim 24, wherein the formoterol free base concentration in the composition is about 10 μg/mL to about 200 μg/mL.

37. The method of claim 36, wherein the formoterol free base concentration in the composition is about 50 μg/mL to about 200 μg/mL.

38. The method of claim 37, wherein the formoterol free base concentration in the composition is about 59 μg/mL.

39. The method of claim 37, wherein the formoterol free base concentration in the composition is about 118 μ/mL.

40. The method of claim 38, wherein the buffer s citrate buffer.

41. The method of claim 38, wherein the buffer concentration is about 5 mM.

42. The method of claim 38, wherein the ionic strength of the composition is about 0.05 to about 0.16.

43. The method of claim 38, wherein the pH of the composition is about 5.0.

44. The method of claim 38, wherein the buffer is citrate buffer; the buffer concentration is about 5 mM; the ionic strength of the composition is about 0.05 to about 0.16; and the pH of the composition is about 5.0.

45. The method of claim 39, wherein the buffer is citrate buffer.

46. The method of claim 39, wherein the buffer concentration is about 5 mM.

47. The method of claim 39, wherein the ionic strength of the composition is about 0.05 to about 0.16.

48. The method of claim 39, wherein the pH of the composition is about 5.0.

49. The method of claim 39, wherein the buffer is citrate buffer; the buffer concentration is about 5 mM; the ionic strength of the composition is about 0.05 to about 0.16; and the pH of on is about 5.0.

50. The method of claim 9, wherein the buffer comprises citric acid/phosphate buffer, acetate buffer, citrate buffer or phosphate buffer.

51. The method of claim 24, wherein the buffer comprises citric acid/phosphate buffer, acetate buffer, citrate buffer or phosphate buffer.

52. The method of claim 1, wherein the steroidal anti-inflammatory agent is beclomethasone dipropionate, beclomethasone monopropionate, flunisolide, triamcinolone acetonide, dexamethasone, tipredane, ciclesonid, rofleponide, mometasone, mometasone furoate,

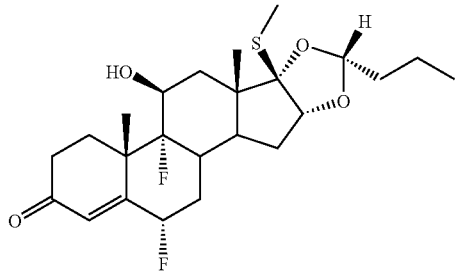

fluticasone or fluticasone propionate, or budesonide, or a pharmaceutically acceptable salt thereof.

53. The method of claim 52, wherein the steroidal anti-inflammatory agent is budesonide or fluticasone propionate, or a pharmaceutically acceptable salt thereof.

54. The method of claim 53, wherein the steroidal anti-inflammatory agent is fluticasone propionate.

55. The method of claim 54, the concentration of fluticasone propionate in the composition is about 5 μg/mL to about 2 mg/mL.

56. The method of claim 55, wherein the concentration of fluticasone propionate in the composition is about 75 μg/mL to about 1000 μg/mL.

57. The method of claim 56, wherein the concentration of fluticasone propionate in the composition is about 125 µg/mL or about 250 µg/mL.

58. The method of claim 44, wherein the steroidal anti-inflammatory agent is budesonide or fluticasone propionate.

59. The method of claim 49, wherein the steroidal anti-inflammatory agent is budesonide or fluticasone propionate.

60. The method of claim 11, wherein the buffer concentration is from about 1 mM to about 50 mM.

61. The method of claim 60, wherein the buffer concentration is about 20 mM.

62. The method of claim 27, wherein the buffer concentration is from about 1 mM to about 50 mM.

63. The method of claim 62, wherein the buffer concentration is about 20 mM.

64. The method of claim 38, wherein the buffer concentration is about 20 mM.

65. The method of claim 38, wherein the buffer is citrate buffer; the buffer concentration is about 20 mM; the ionic strength of the composition is about 0.05 to about 0.16; and the pH of the composition is about 5.0.

66. The method of claim 39, wherein the buffer concentration is about 20 mM.

67. The method of claim 39, wherein the buffer is citrate buffer; the buffer concentration is about 20 mM; the ionic strength of the composition is about 0.05 to about 0.16; and the pH of the composition is about 5.0.

68. The method of claim 1, wherein the composition further comprises an anticholinergic agent.

69. The method of claim 68, wherein the anticholinergic agent is ipratropium bromide, oxitropium bromide, atropine methyl nitrate, tiotropium bromide or glycopyrronium bromide.

70. The method of claim 69, wherein the anticholinergic agent is ipratropium bromide.

71. The method of claim 70, wherein the ipratropium bromide concentration in the composition is about 5 µg/mL to about 5 mg/mL.

72. The method of claim 1, wherein the bronchoconstrictive disorder is asthma, bronchial asthma, allergic asthma, intrinsic asthma, late asthma, airway hyper-responsiveness, chronic obstructive pulmonary diseases (COPDs), COPD associated with cigarette smoking, COPD associated with infections, COPD associated with environmental pollution, COPD associated with occupational dust exposure, chronic bronchitis, emphysema, cor pulmonale associated with pulmonary hypertension, cor pulmonale associated with right ventricular hypertrophy, or cor pulmonale associated with right heart failure.

73. The method of claim 38, wherein the bronchoconstrictive disorder is asthma, bronchial asthma, allergic asthma, intrinsic asthma, late asthma, airway hyper-responsiveness, chronic obstructive pulmonary diseases (COPDs), COPD associated with cigarette smoking, COPD associated with infections, COPD associated with environmental pollution, COPD associated with occupational dust exposure, chronic bronchitis, emphysema, cor pulmonale associated with pulmonary hypertension, cor pulmonale associated with right ventricular hypertrophy, or cor pulmonale associated with right heart failure.

74. The method of claim 39, wherein the bronchoconstrictive disorder is asthma, bronchial asthma, allergic asthma, intrinsic asthma, late asthma, airway hyper-responsiveness, chronic obstructive pulmonary diseases (COPDs), COPD associated with cigarette smoking, COPD associated with infections, COPD associated with environmental pollution, COPD associated with occupational dust exposure, chronic bronchitis, emphysema, cor pulmonale associated with pulmonary hypertension, cor pulmonale associated with right ventricular hypertrophy, or cor pulmonale associated with right heart failure.

75. The method of claim 1, wherein the formoterol is formoterol fumarate dihydrate; and the steroidal anti-inflammatory agent is fluticasone propionate.

76. The method of claim 75, wherein the concentration of fluticasone propionate in the composition is about 75 µg/mL to about 1000 µg/mL.

77. The method of claim 76, wherein the concentration of fluticasone propionate in the composition is about 250 µg/mL to about 1000 µg/mL.

78. The method of claim 76, wherein the concentration of fluticasone propionate in the composition is about 125 µg/mL to about 250 µg/mL.

79. The method of claim 75, wherein the composition further comprises a tonicity adjusting agent, a suspension stabilizer, and the pharmaceutically suitable fluid comprises a buffer.

80. The method of claim 79, wherein the tonicity adjusting agent comprises sodium chloride and sodium edetate, the suspension stabilizer is Polysorbate 80, and the buffer is a sodium citrate buffer.

81. The method of claim 1, wherein the packaged pharmaceutical composition is packaged in a vial.

82. A method for the treatment or amelioration of one or more symptoms of bronchoconstrictive disorders, comprising: (i) providing a packaged pharmaceutical composition comprising formoterol, or a pharmaceutically acceptable salt or hydrate thereof in solution, the pharmaceutical composition being in a pharmacologically suitable fluid comprising water that is propellant-free, wherein: the composition has an estimated shelf-life of greater than 1 month usage time at 25° C. and greater than or equal to 1 year storage time when stored at 5° C. whereby greater than 90% of the initial amount of formoterol in the compositions remains at such time; the formoterol free base concentration is about 5 µg/mL to about 200 µg/mL, whereby the composition is formulated at a concentration for direct administration to a human in need thereof; (ii) without dilution, directly administering an effective amount of the composition as provided to a human; and (ii) simultaneously with, prior to, or subsequent to administering the formoterol composition, administering an effective amount of a pharmaceutical composition comprising a steroidal anti-inflammatory agent, or a pharmaceutically acceptable salt thereof in suspension, in a pharmacologically acceptable carrier.

83. The method of claim 82, wherein the steroidal anti-inflammatory agent is beclomethasone dipropionate, beclomethasone monopropionate, flunisolide, triamcinolone acetonide, dexamethasone, tipredane, ciclesonid, rofleponide, mometasone, mometasone furoate,

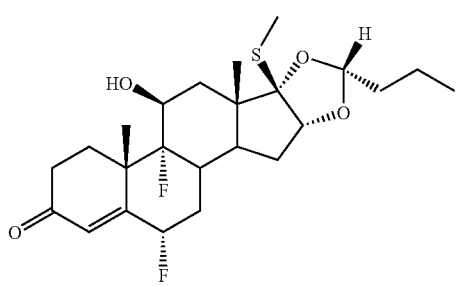

fluticasone or fluticasone propionate, or budesonide, or a pharmaceutically acceptable salt thereof.

84. The method of claim 83, wherein the steroidal anti-inflammatory agent is fluticasone propionate or budesonide, or a pharmaceutically acceptable salt thereof.

85. The method of claim 83, wherein the steroidal anti-inflammatory agent is fluticasone propionate, or a pharmaceutically acceptable salt thereof.

86. The method of claim 82, wherein the composition containing formoterol also contains the steroidal anti-inflammatory agent, or a pharmaceutically acceptable salt thereof, whereby the formoterol, or a pharmaceutically acceptable salt or hydrate thereof, and the steroidal anti-inflammatory agent, or a pharmaceutically acceptable salt thereof, are administered simultaneously.

87. The method of claim 82, wherein the packaged pharmaceutical composition is packaged in a vial.

88. A method for the treatment or amelioration of one or more symptoms of bronchoconstrictive disorders, comprising: providing a pharmaceutical composition formulated and packaged for single dosage administration, wherein: the composition contains: (i) formoterol, or a pharmaceutically acceptable salt or hydrate thereof in solution; and (ii) a steroidal anti-inflammatory agent, or a pharmaceutically acceptable salt thereof in suspension; in a pharmacologically suitable fluid comprising water that is propellant-free; the composition as formulated has an estimated shelf-life of greater than 1 month usage time at 25° C. and greater than or equal to 1 year storage time when stored at 5° C. whereby greater than 90% of the initial amount of formoterol in the compositions remains at such time; and the formoterol free base concentration is about 5 µg/mL to about 200 µg/mL, whereby the composition is formulated for direct administration to a human in need thereof; and without dilution, directly administering via nebulization an effective amount of the composition as provided to a subject in need of such treatment.

89. The method of claim 88, wherein the packaged pharmaceutical composition is packaged in a vial.

* * * * *

UNITED STATES PATENT AND TRADEMARK OFFICE
CERTIFICATE OF CORRECTION

PATENT NO. : 8,623,851 B2  
APPLICATION NO. : 12/625328  
DATED : January 7, 2014  
INVENTOR(S) : Partha S. Banerjee et al.

Page 1 of 2

It is certified that error appears in the above-identified patent and that said Letters Patent is hereby corrected as shown below:

In the Claims

Claim 1, col. 21, l. 44 should read "80%" instead of "90%."

Claim 1, col. 21, l. 47 should read "about 118 µg/mL" instead of "about 200 µg/mL."

Claim 2, col. 21, l. 51 should read "90%" instead of "80%."

Claim 6 at col. 21, l. 64, "boric acid" should be deleted.

Claim 6 at col. 22, l. 7, "sodium borate" should be deleted.

Claim 6 at col. 22, l. 12, "triethanolamine" should be deleted.

Claim 9 at col. 22, l. 19, "borate" should be deleted.

Claim 9 at col. 22, ll. 20-21, "citrate-phosphate-borate (Teorell-Stanhagen)" should be deleted.

Claim 9 at col. 22, ll. 22-23, "BIS-TRIS (bis(2-hydroxyethyl)iminotris(hydroxymethyl)methane" should be deleted.

Claim 9 at col. 22, ll. 27-29, "BIS-TRIS PROPANE (1,3-bis(tris(hydroxymethyl)methylamino)propane)" should be deleted.

Claim 9 at col. 22, l. 37, "tris(hydroxymethylaminomethane" should be deleted.

Claim 9 at col. 22, l. 40, "TEA (triethanolamine)" should be deleted.

Claim 16 should be deleted.

Signed and Sealed this  
Twenty-fifth Day of November, 2014

Michelle K. Lee  
*Deputy Director of the United States Patent and Trademark Office*

CERTIFICATE OF CORRECTION (continued)

U.S. Pat. No. 8,623,851 B2

Claim 17 should depend from claim 1 instead of from claim 16.

Claims 20 and 21 should be deleted.

Claim 25 at col. 23, l. 14, "borate" should be deleted.

Claim 25 at col. 23, ll. 15-16, "citrate-phosphate-borate (Teorell-Stanhagen)" should be deleted.

Claim 25 at col. 23, ll. 17-18, "BIS-TRIS (bis(2-hydroxyethyl)iminotris-(hydroxymethyl)methane" should be deleted.

Claim 25 at col. 23, ll. 22-24, "BIS-TRIS PROPANE (1,3-bis(tris(hydroxymethyl)methylamino)propane" should be deleted.

Claim 25 at col. 23, l. 32, "tris(hydroxymethylaminomethane" should be deleted.

Claim 32 should be deleted.

Claim 33 should depend from claim 24 instead of claim 32.

Claim 36 at col. 23, l. 64 should read "about 118 µg/mL" instead of "about 200 µg/mL."

Claim 37, col. 23, l. 67 should read "about 118 µg/mL" instead of "about 200 µg/mL."

Claim 82, col. 26, ll. 37-38, should read "about 118 µg/mL" instead of "about 200 µg/mL."

UNITED STATES PATENT AND TRADEMARK OFFICE
CERTIFICATE OF CORRECTION

Page 1 of 2

PATENT NO. : 8,623,851 B2
APPLICATION NO. : 12/625328
DATED : January 7, 2014
INVENTOR(S) : Partha S. Banerjee et al.

It is certified that error appears in the above-identified patent and that said Letters Patent is hereby corrected as shown below:

On the title page, under abstract "89 Claims, No Drawing Sheets" should read -- 85 Claims, No Drawing Sheets --.

In the Claims

Claim 1, col. 21, l. 44 should read "80%" instead of "90%.".

Claim 1, col. 21, l. 47 should read "about 118 μg/mL" instead of "about 200 μg/mL.".

Claim 2, col. 21, l. 51 should read "90%" instead of "80%.".

Claim 6 at col. 21, l. 64, "boric acid" should be deleted.

Claim 6 at col. 22, l. 7, "sodium borate" should be deleted.

Claim 6 at col. 22, l. 12, "triethanolamine" should be deleted.

Claim 9 at col. 22, l. 19, "borate" should be deleted.

Claim 9 at col. 22, ll. 20-21, "citrate-phosphate-borate (Teorell-Stanhagen)" should be deleted.

Claim 9 at col. 22, ll. 22-23, "BIS-TRIS (bis(2-hydroxyethyl)iminotris(hydroxymethyl)methane" should be deleted.

Claim 9 at col. 22, ll. 27-29, "BIS-TRIS PROPANE (1,3-bis(tris(hydroxymethyl)methylamino)propane)" should be deleted.

This certificate supersedes the Certificate of Correction issued November 25, 2014.

Signed and Sealed this
Twenty-third Day of December, 2014

Michelle K. Lee
*Deputy Director of the United States Patent and Trademark Office*

CERTIFICATE OF CORRECTION (continued)

Claim 9 at col. 22, l. 37, "tris(hydroxymethylaminomethane" should be deleted.

Claim 9 at col. 22, l. 40, "TEA (triethanolamine)" should be deleted.

Claim 16 should be deleted.

Claim 17 should depend from claim 1 instead of from claim 16.

Claims 20 and 21 should be deleted.

Claim 25 at col. 23, l. 14, "borate" should be deleted.

Claim 25 at col. 23, ll. 15-16, "citrate-phosphate-borate (Teorell-Stanhagen)" should be deleted.

Claim 25 at col. 23, ll. 17-18, "BIS-TRIS (bis(2-hydroxyethyl)iminotris-(hydroxymethyl)methane" should be deleted.

Claim 25 at col. 23, ll. 22-24, "BIS-TRIS PROPANE (1,3-bis(tris(hydroxymethyl)methylamino)propane" should be deleted.

Claim 25 at col. 23, l. 32, "tris(hydroxymethylaminomethane" should be deleted.

Claim 32 should be deleted.

Claim 33 should depend from claim 24 instead of claim 32.

Claim 36 at col. 23, l. 64 should read "about 118 µg/mL" instead of "about 200 µg/mL.".

Claim 37, col. 23, l. 67 should read "about 118 µg/mL" instead of "about 200 µg/mL.".

Claim 82, col. 26, ll. 37-38, should read "about 118 µg/mL" instead of "about 200 µg/mL.".